(12) United States Patent
Prudhomme et al.

(10) Patent No.: US 7,001,906 B2
(45) Date of Patent: Feb. 21, 2006

(54) PYRIDO-PYRIDO-PYRROLO PYRROLO-INDOLE AND PYRIDO-PYRROLO PYRROLO CARBAZOLE DERIVATIVES, METHOD FOR THE PRODUCTION THEREOF AND PHARMACEUTICAL COMPOSITIONS CONTAINING SAID DERIVATIVES

(75) Inventors: Michelle Prudhomme, Clermont-Ferrand (FR); Christelle Marminon, Maisons-Laffitte (FR); Sylvain Routier, Tigy (FR); Gérard Coudert, Saint Denis en Val (FR); Jean-Yves Merour, Olivet (FR); John Hickman, Paris (FR); Alain Pierre, Les Alluets le Roi (FR); Pierre Renard, Le Chesnay (FR); Bruno Pfeiffer, Saint Leu la Foret (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 32 days.

(21) Appl. No.: 10/481,991

(22) PCT Filed: Jun. 28, 2002

(86) PCT No.: PCT/FR02/02250

§ 371 (c)(1),
(2), (4) Date: Dec. 24, 2003

(87) PCT Pub. No.: WO03/002563

PCT Pub. Date: Jan. 9, 2003

(65) Prior Publication Data

US 2004/0152721 A1 Aug. 5, 2004

(30) Foreign Application Priority Data

Jun. 29, 2001 (FR) .................................. 0108615

(51) Int. Cl.
| | | |
|---|---|---|
| *A61K 31/4985* | (2006.01) | |
| *A61K 31/437* | (2006.01) | |
| *C07D 491/22* | (2006.01) | |
| *C07D 405/14* | (2006.01) | |

(52) U.S. Cl. ...................... 514/250; 544/338; 546/41; 546/113; 514/279; 514/300

(58) Field of Classification Search ................ 514/250, 514/279, 300; 544/338; 546/41, 113
See application file for complete search history.

(56) References Cited

U.S. PATENT DOCUMENTS 6,569,858 B1 * 5/2003 Prudhomme et al. ....... 514/250

FOREIGN PATENT DOCUMENTS

| EP | 1 101 770 | 5/2001 |
|---|---|---|
| WO | WO 92 18507 | 10/1992 |
| WO | WO 95 07910 | 3/1995 |
| WO | WO 96 04906 | 2/1996 |
| WO | WO 96 11933 | 4/1996 |
| WO | WO 00 13015 | 3/2000 |

OTHER PUBLICATIONS

Anizon F, et al.: "Syntheses, Biochemical and Biological Evaluation of Staurosporine Analogues from the Microbial Metabolite Rebeccamycin" Bioorganic & Medicinal Chemistry, Elsevier Science Ltd, GB, vol. 6, No. 9, 1998, pp. 1597-1604.

* cited by examiner

*Primary Examiner*—Charanjit S. Aulakh
(74) *Attorney, Agent, or Firm*—Hueschen and Sage

(57) ABSTRACT

Compounds of formula (I):

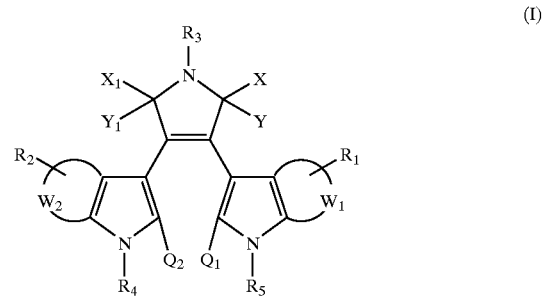

wherein:
$W_1$ and $W_2$, together with the carbon atoms to which they are bonded, represent a phenyl group or a pyridyl group, and at least one of the groups $W_1$ or $W_2$ represents a pyridyl group,
$R_1$ and $R_2$ each represent a group of formula U-V as defined in the description,
X and $X_1$ each represent a hydrogen atom or a hydroxy, alkoxy, mercapto or alkylthio group,
Y and $Y_1$ each represent a hydrogen atom,
or X and Y, $X_1$ and $Y_1$, together with the carbon atom carrying them, represent a carbonyl or thiocarbonyl group,
$R_4$ and $R_5$ are as defined in the description,
$Q_1$, $Q_2$ represent a hydrogen atom, or
$Q_1$ and $Q_2$, together with the carbon atoms carrying them, form an aromatic bond.

Medicaments.

20 Claims, No Drawings

PYRIDO-PYRIDO-PYRROLO PYRROLO-INDOLE AND PYRIDO-PYRROLO PYRROLO CARBAZOLE DERIVATIVES, METHOD FOR THE PRODUCTION THEREOF AND PHARMACEUTICAL COMPOSITIONS CONTAINING SAID DERIVATIVES

The present invention relates to new pyrido-pyrido-pyrrolo[3,2-g]pyrrolo[3,4-e]indole and pyrido-pyrrolo[2,3-a]pyrrolo[3,4-c]carbazole compounds, to a process for their preparation and to pharmaceutical compositions containing them.

Anti-cancer therapeutic requirements call for the constant development of new antiproliferative agents with the aim of obtaining medicaments that are simultaneously more active and better tolerated. The compounds of the present invention especially have anti-tumour properties, making them of use in the treatment of cancers.

Patent Applications WO95/07910 and WO96/04906 describe indole compounds, claiming them, on the one hand, for their antiviral activity and, on the other hand, for the treatment and prevention of restenosis. Patent Applications WO00/47583, WO97/21677 and WO96/11933 describe cyclopenta[g]pyrrolo[3,4-e]indole compounds fused, by the indole moiety and the cyclopentene moiety of the compounds, to an aromatic or non-aromatic cyclic system, and optionally containing hetero atoms. Those compounds have pharmacological activities making them especially useful in the treatment of cancerous cells.

The compounds of the present Application differ greatly from those described in the prior art and possess particular pharmacological properties and, especially, surprising in vivo and in vitro activity with respect to various cell lines, making them of use in the treatment of cancers.

More specifically, the present invention relates to compounds of formula (I):

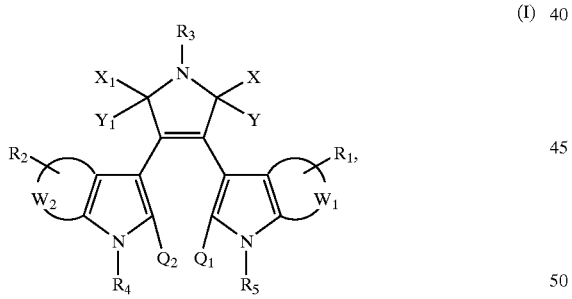

(I)

wherein:
$W_1$, $W_2$ each represent, together with the carbon atoms to which they are bonded, a phenyl group or a pyridyl group, wherein at least one of the groups $W_1$ or $W_2$ represents a pyridyl group, $R_1$, $R_2$, which may be the same or different, represent, each independently of the other, a group of formula U-V wherein:
  U represents a single bond or a linear or branched ($C_1$–$C_6$)alkylene chain optionally substituted by one or more identical or different groups selected from halogen and hydroxy, and/or optionally containing one or more unsaturated bonds,
  V represents a group selected from hydrogen and halogen atoms and cyano, nitro, azido, linear or branched($C_1$–$C_6$)alkyl, aryl, aryl-($C_1$–$C_6$)alkyl (wherein the alkyl moiety may be linear or branched), hydroxy, linear or branched ($C_1$–$C_6$) alkoxy, aryloxy, aryl-($C_1$–$C_6$)alkoxy (wherein the alkoxy moiety may be linear or branched), formyl, carboxy, aminocarbonyl, $NR_6R_7$, —C(O)-$T_1$, —C(O)—$NR_6$-$T_1$, —$NR_6$—C(O)-$T_1$, —O—C(O)-$T_1$, —C(O)—O-$T_1$, —O-$T_2$-$NR_6R_7$, —O-$T_2$-$OR_6$, —O-$T_2$-$CO_2R_6$, —$NR_6$-$T_2$-$NR_6R_7$, —$NR_6$-$T_2$-$OR_6$, —$NR_6$-$T_2$-$CO_2R_6$ and —S(O)$_t$—$R_6$ groups, wherein:
  $R_6$ and $R_7$, which may be the same or different, each represent a group selected from a hydrogen atom and linear or branched ($C_1$–$C_6$)alkyl groups, aryl groups and aryl-($C_1$–$C_6$)alkyl groups (wherein the alkyl moiety may be linear or branched), or $R_6$+$R_7$, together with the nitrogen atom carrying them, form a saturated, monocyclic or bicyclic heterocycle of 5 to 10 atoms optionally containing, in the cyclic system, a second hetero atom selected from oxygen and nitrogen, and being optionally substituted by a group selected from linear or branched ($C_1$–$C_6$)alkyl, aryl, aryl-($C_1$–$C_6$)alkyl wherein the alkyl moiety is linear or branched, hydroxy, linear or branched ($C_1$–$C_6$) alkoxy, amino, linear or branched mono-($C_1$–$C_6$) alkylamino, and di-($C_1$–$C_6$)alkylamino wherein each alkyl moiety may be linear or branched,
  $T_1$ represents a group selected from linear or branched ($C_1$–$C_6$)alkyl, aryl, aryl-($C_1$–$C_6$)alkyl in which the alkyl moiety is linear or branched, a linear or branched ($C_1$–$C_6$)alkylene chain substituted by a group selected from —$OR_6$, —$NR_6R_7$, —$CO_2R_6$, —C(O)$R_6$ and —C(O)$NR_6R_7$ wherein $R_6$ and $R_7$ are as defined hereinbefore, and a linear or branched ($C_2$–$C_6$)alkenylene chain substituted by a group selected from —$OR_6$, —$NR_6R_7$, —$CO_2R_6$, —C(O)$R_6$ and —C(O)$NR_6R_7$ wherein $R_6$ and $R_7$ are as defined hereinbefore,
  $T_2$ represents a linear or branched ($C_1$–$C_6$)alkylene chain,
  t represents an integer of from 0 to 2 inclusive, $R_3$ represents a group selected from a hydrogen atom and linear or branched ($C_1$–$C_6$)alkyl, aryl, aryl-($C_1$–$C_6$) alkyl (wherein the alkyl moiety may be linear or branched), cycloalkyl, cycloalkyl-($C_1$–$C_6$)alkyl (wherein the alkyl moiety may be linear or branched), —$OR_6$, —$NR_6R_7$, —O-$T_2$-$NR_6R_7$, —$NR_6$-$T_2$-$NR_6R_7$, linear or branched ($C_1$–$C_6$)hydroxyalkylamino, di(($C_1$–$C_6$)hydroxyalkyl)amino (wherein each alkyl moiety may be linear or branched), —C(O)—$R_6$ and —NH—C(O)—$R_6$ groups and a linear or branched ($C_1$–$C_6$)alkylene chain substituted by one or more identical or different groups selected from halogen atoms and cyano, nitro, —$OR_6$, —$NR_6R_7$, —$CO_2R_6$, —C(O)$R_6$, linear or branched ($C_1$–$C_6$)hydroxyalkylamino, di(($C_1$–$C_6$)hydroxyl-alkyl)amino (wherein each alkyl moiety may be linear or branched), and —C(O)—$NHR_6$ groups, the groups $R_6$, $R_7$ and $T_2$ being as defined hereinbefore, X represents a group selected from a hydrogen atom and hydroxy, linear or branched ($C_1$–$C_6$)alkoxy, mercapto and linear or branched ($C_1$–$C_6$)alkylthio groups, Y represents a hydrogen atom, or X and Y, together with the carbon atom carrying them, form a carbonyl or thiocarbonyl group, X₁ represents a group selected from a hydrogen atom and hydroxy, linear or branched (C₁–C₆)alkoxy, mercapto and linear or branched (C₁–C₆)alkylthio groups, Y₁ represents a hydrogen atom, or X₁ and Y₁, together with the carbon atom carrying them, form a carbonyl or thiocarbonyl group, Q₁, Q₂ represent a hydrogen atom, or Q₁ and Q₂, together with the carbon atoms carrying them, form an aromatic bond, R₄ represents a group of formula (a):

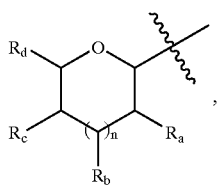

(a)

wherein:
Rₐ, R_b and R_c, which may be the same or different, represent, each independently of the others, a group selected from a hydrogen atom and a halogen atom, and hydroxy, linear or branched (C₁–C₆)alkoxy, aryloxy, aryl-(C₁–C₆)alkoxy (wherein the alkoxy moiety is linear or branched), linear or branched (C₁–C₆) alkyl, aryl-(C₁–C₆)alkyl (wherein the alkyl moiety is linear or branched), aryl, —NR₆R₇ (wherein R₆ and R₇ are as defined hereinbefore), azido, —N=NR₆ (wherein R₆ is as defined hereinbefore), and —O—C(O)—R₈ groups, wherein R₈ represents a linear or branched (C₁–C₆)alkyl (optionally substituted by one or more groups selected from halogen, hydroxy, amino, linear or branched (C₁–C₆)alkylamino, and di-(C₁–C₆)alkylamino wherein each alkyl moiety may be linear or branched), aryl, aryl-(C₁–C₆)alkyl (wherein the alkyl moiety is linear or branched), cycloalkyl or heterocycloalkyl group, R_d represents a methylidene group or a group of formula -U₁-Rₐ wherein U₁ represents a single bond or a methylene group and Rₐ is as defined hereinbefore, n has the value 0 or 1, R₅ represents a group selected from a hydrogen atom and linear or branched (C₁–C₆)-alkyl groups, aryl-(C₁–C₆) alkyl groups (wherein the alkyl moiety is linear or branched), arylsulphonyl groups, linear or branched (C₁–C₆)alkyloxycarbonyl groups, —OR₆ and —C(O)—R₆ groups (wherein R₆ is as defined hereinbefore), R₄ and R₅ together represent, with the proviso that in this case Q₁ and Q₂ together form an aromatic bond, a group of formula (b) or (c):

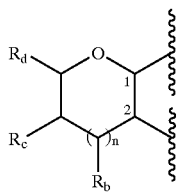

(b)

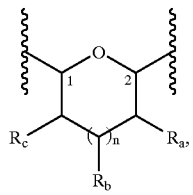

(c)

wherein:
carbon atom 1 is bonded to the nitrogen atom of the ring (A) and carbon atom 2 is bonded to the nitrogen atom of the ring (B), Rₐ, R_b, R_c and R_d are as defined hereinbefore, n has the value 0 or 1, to their enantiomers and diastereoisomers, and to addition salts thereof with a pharmaceutically acceptable acid or base, aryl being understood to mean a phenyl, naphthyl, dihydronaphthyl, tetrahydronaphthyl, indenyl or indanyl group, each of those groups being optionally substituted by one or more identical or different groups selected from halogen, linear or branched (C₁–C₆)alkyl, linear or branched (C₁–C₆) trihaloalkyl, hydroxy, linear or branched (C₁–C₆)alkoxy, and amino optionally substituted by one or two linear or branched (C₁–C₆)alkyl groups.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fuimaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preferred compounds of the invention are those wherein X and Y, together with the carbon atom carrying them, form a carbonyl group and X₁ and Y₁, together with the carbon atom carrying them, form a carbonyl group. According to an advantageous embodiment, preferred compounds of the invention are compounds of formula (I) that correspond in particular to formula (IA):

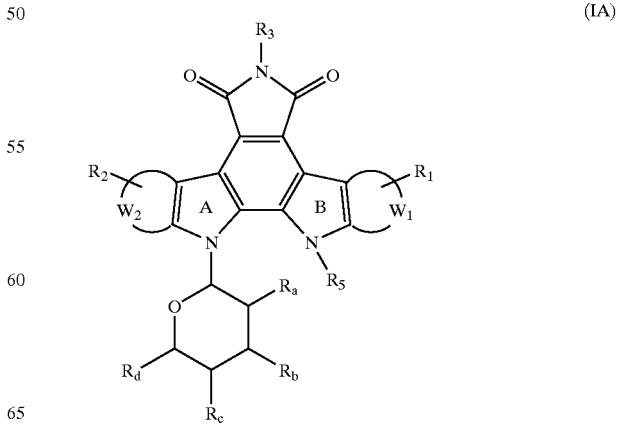

(IA)

wherein $R_1$, $R_2$, $R_3$, $R_5$, $R_a$, $R_b$, $R_c$, $R_d$, $W_1$ and $W_2$ are as defined for formula (I).

According to a second advantageous embodiment, preferred compounds of the invention are compounds of formula (I) that correspond in particular to formula (IB):

(IB)

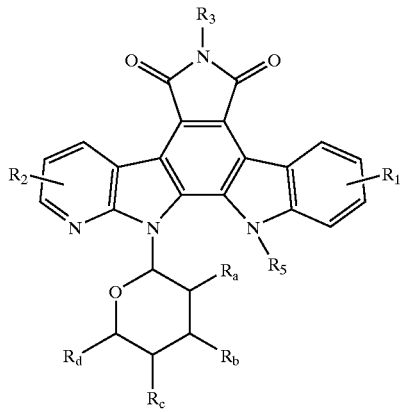

wherein $R_1$, $R_2$, $R_3$, $R_5$, $R_a$, $R_b$, $R_c$ and $R_d$ are as defined for formnula (I).

According to a third advantageous embodiment, preferred compounds of the invention are compounds of formula (I) that correspond in particular to formula (IC):

(IC)

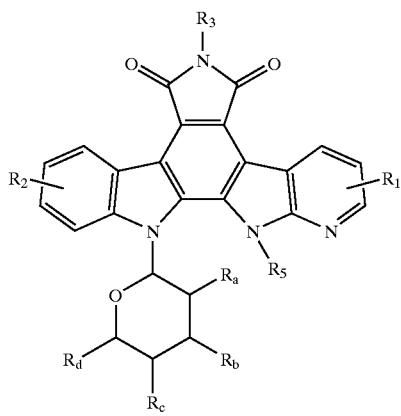

wherein $R_1$, $R_2$, $R_3$, $R_5$, $R_a$, $R_b$, $R_c$ and $R_d$ are as defined for formula (I).

According to a fourth advantageous embodiment, preferred compounds of the invention are compounds of formula (I) that correspond in particular to formula (ID):

(ID)

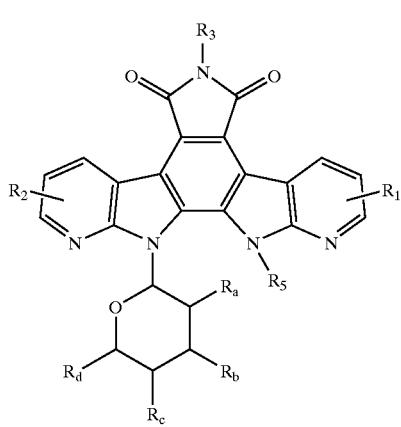

wherein $R_1$, $R_2$, $R_3$, $R_5$, $R_a$, $R_b$, $R_c$ and $R_d$ are as defined for formula (I).

According to a fifth advantageous embodiment, preferred compounds of the invention are compounds of formula (IE):

(IE)

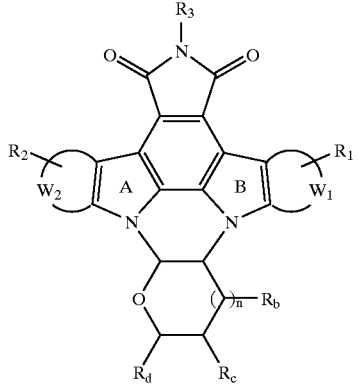

wherein $R_1$, $R_2$, $R_3$, $R_5$, $R_b$, $R_c$, $R_d$, n, $W_1$ and $W_2$ are as defined for formula (I).

According to a sixth advantageous embodiment, preferred compounds of the invention are compounds of formula (IF):

(IF)

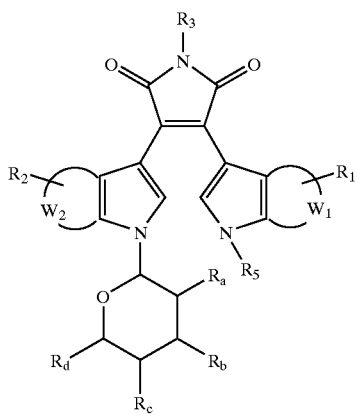

wherein $R_1$, $R_2$, $R_3$, $R_5$, $R_a$, $R_b$, $R_c$, $R_d$, $W_1$ and $W_2$ are as defined for formula (I).

According to a seventh advantageous embodiment, preferred compounds of the invention are compounds of formnula (IG):

(IG)

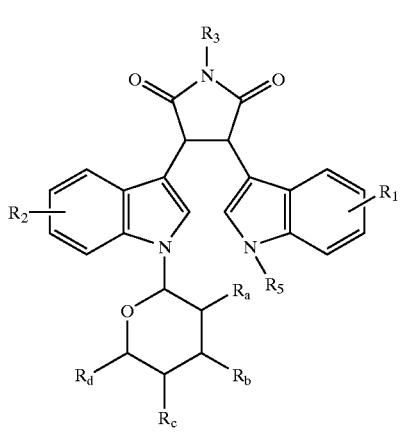

wherein $R_1$, $R_2$, $R_3$, $R_5$, $R_a$, $R_b$, $R_c$ and $R_d$ are as defined for formula (I).

According to a ninth advantageous embodiment, preferred compounds of the invention are compounds of formula (IH):

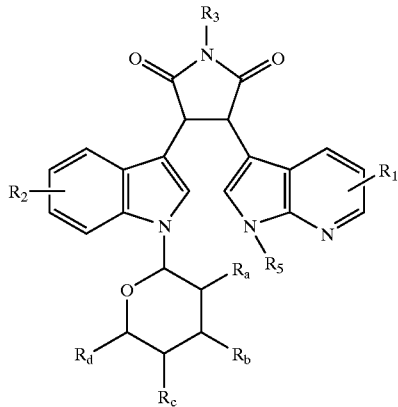

(IH)

wherein $R_1$, $R_2$, $R_3$, $R_5$, $R_a$, $R_b$, $R_d$ are as defined for formula (I).

According to a ninth advantageous embodiment, preferred compounds of the invention are compounds of formula (IJ):

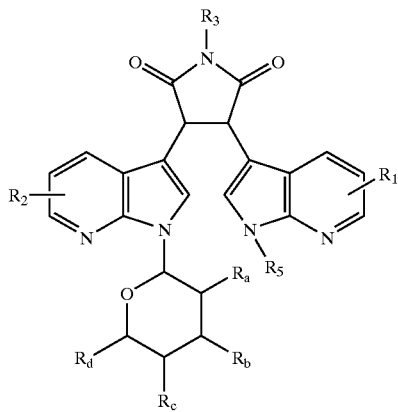

(IJ)

wherein $R_1$, $R_2$, $R_3$, $R_5$, $R_a$, $R_b$, $R_c$ and $R_d$ are as defined for formula (I).

Advantageously, the pyridine ring that is preferred according to the invention is the unsubstituted ring.

Advantageously, the group R4 that is preferred according to the invention is the glucopyranosyl group of formula:

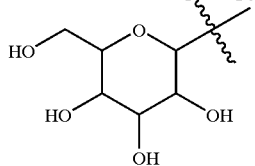

Very advantageously, the group $R_2$ that is preferred according to the invention is the hydrogen atom.

The groups $R_1$ that are preferred according to the invention are the hydrogen atom, halogen atoms and the nitro group.

Preferred compounds according to the invention are:
6-methyl-13-(β-glucopyranosyl)-12,13-dihydro-5H-pyrido[3',2':4,5]pyrrolo[2,3-a]-pyrrolo[3,4-c]carbazole-5,7(6H)-dione,
6-methyl-12-(β-glucopyranosyl)-12,13-dihydro-5H-pyrido[2,3-b]pyrido[3',2':4,5]-pyrrolo[3,2-g]pyrrolo[3,4-e]indole-5,7(6H)-dione,
9-bromo-6-methyl-13-(β-D-glucopyranosyl)-12,13-dihydro-5H-pyrido[3',2':4,5]-pyrrolo[2,3-a]pyrrolo[3,4-c]carbazole-5,7(6H)-dione,
13-(β-D-glucopyranosyl)-12,13-dihydro-5H-pyrido[3',2':4,5]pyrrolo[2,3-a]pyrrolo-[3,4-c]carbazole-5,7(6H)-dione,
9-nitro-13-(β-D-glucopyranosyl)-12,13-dihydro-5H-pyrido[3',2':4,5]pyrrolo[2,3-a]-pyrrolo[3,4-c]carbazole-5,7(6H)-dione,
12-(β-D-glucopyranosyl)-12,13-dihydro-5H-pyrido[2,3-b]pyrido[3',2':4,5]pyrrolo-[3,2-g]pyrrolo[3,4-e]indole-5,7(6H)-dione
and 1-methyl-3-[1-(β-D-glucopyranosyl)-1H-pyrrolo[2,3-b]pyrid-3-yl]-4-(1H-pyrrolo[2,3-b]pyrid-3-yl)-1H-pyrrole-2,5-dione.

The enantiomers and diastereoisomers and addition salts with a pharmaceutically acceptable acid or base of the preferred compounds form an integral part of the invention.

The present invention relates also to a process for the preparation of compounds of formula (I), which process is characterised in that there is used as starting material a compound of formula (II):

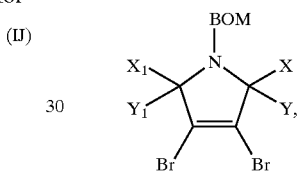

(II)

wherein BOM represents a benzyloxymethyl group and X, Y, $X_1$ and $Y_1$ are as defined for formula (I), which compound of formula (II) is treated with an alkylmagnesium halide in the presence of a compound of formula (III):

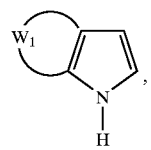

(III)

wherein $W_1$ is as defined for formula (I), to yield the compound of formula (IV):

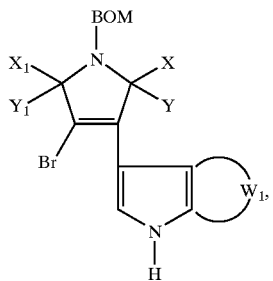

(IV)

wherein X, Y, $X_1$, $Y_1$, BOM and $W_1$ are as defined hereinbefore, which compound of formula (IV) is reacted with benzenesulphonyl chloride in the presence of sodium hydride to yield the compound of formula (V):

(V)

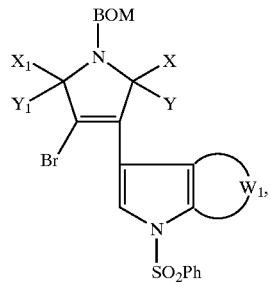

wherein BOM, X, Y, $X_1$, $Y_1$ and $W_1$ are as defined hereinbefore, which compound of formula (V) is reacted, in the presence of lithium hexamethyldisilazane, with a compound of formula (VI):

(VI)

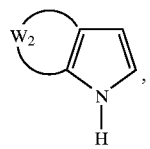

wherein $W_2$ is as defined for formula (I), to yield the compound of formula (VII):

(VII)

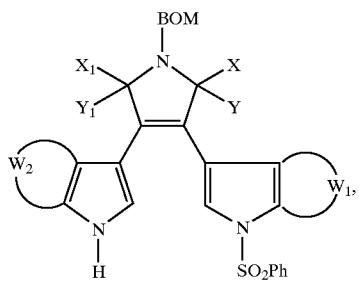

wherein BOM, X, Y, $X_1$, $Y_1$, $W_1$ and $W_2$ are as defined hereinbefore, which compound of formula (VII) is reacted, in the presence of triphenylphosphine and diethyl azodicarboxylate, with a compound of formula ($a_1$):

($a_1$)

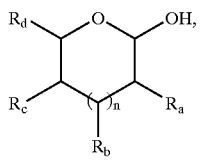

wherein $R_a$, $R_b$, $R_c$, $R_d$ and n are as defined for formula (I), to yield the compound of formula (I/a), a particular case of the compounds of formula (I):

(I/a)

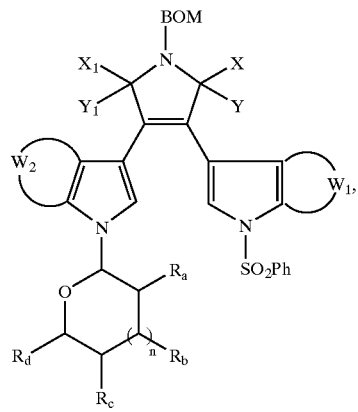

wherein BOM, X, Y, $X_1$, $Y_1$, $W_1$, $W_2$, $R_a$, $R_b$, $R_c$, $R_d$ and n are as defined hereinbefore, which compound of formula (I/a) is treated with a solution of tetrabutylammonium fluoride in tetrahydrofuran to yield the compound of formula (I/b), a particular case of the compounds of formula (I):

(I/b)

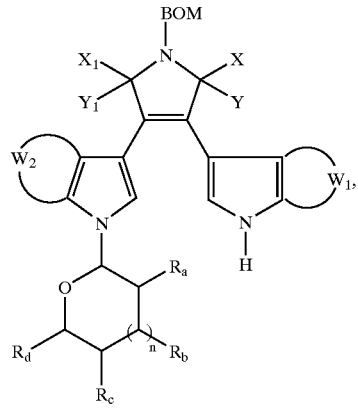

wherein BOM, X, Y, $X_1$, $Y_1$, $W_1$, $W_2$, $R_a$, $R_b$, $R_c$, $R_d$ and n are as defined hereinbefore, which compound of formula (I/b) is irradiated with a UV lamp, in the presence of iodine, in a non-polar and aprotic solvent, to yield the compound of formula (I/c), a particular case of the compounds of formula (I):

(I/c)

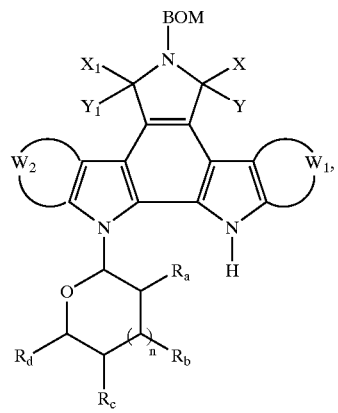

wherein BOM, X, Y, $X_1$, $Y_1$, $W_1$, $W_2$, $R_a$, $R_b$, $R_c$, $R_d$ and n are as defined hereinbefore, the totality of the compounds of formulae (I/b) and (I/c) forming the compounds of formula (I/d):

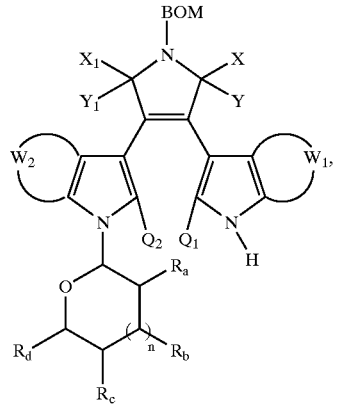

(I/d)

wherein BOM, X, Y, $X_1$, $Y_1$, $W_1$, $W_2$, $R_a$, $R_b$, $R_c$, $R_d$ and n are as defined hereinbefore and $Q_1$ and $Q_2$ are as defined for formula (I), which compound of formnula (I/d) is:
either treated, in a basic medium, with a compound of formula (VIII):

$R'_5$-Hal        (VIII), wherein Hal represents a halogen atom and $R'_5$ is as defined for $R_5$ in formula (I) except for the meaning of a hydrogen atom, to yield the compound of formula (I/e), a particular case of the compounds of formula (I):

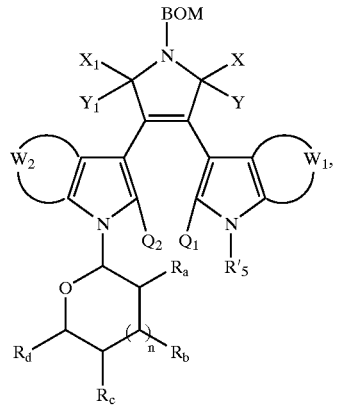

(I/e)

wherein BOM, X, Y, $X_1$, $Y_1$, $W_1$, $W_2$, $R_a$, $R_b$, $R_c$, $R_d$, n, $Q_1$, $Q_2$ and $R'_5$ are as defined hereinbefore, the totality of the compounds of formulae (I/d) and (I/e) forming the compounds of formula (I/f):

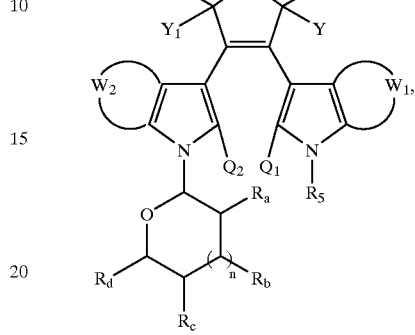

(I/f)

wherein BOM, X, Y, $X_1$, $Y_1$, $W_1$, $W_2$, $R_a$, $R_b$, $R_c$, $R_d$, n, $Q_1$ and $Q_2$ are as defined hereinbefore and $R_5$ is as defined for formula (I), which compound of formula (I/f) is placed under a hydrogen atmosphere in the presence of palladium-on-carbon, in a polar solvent, to yield the compound of formula (I/g), a particular case of the compounds of formula (I):

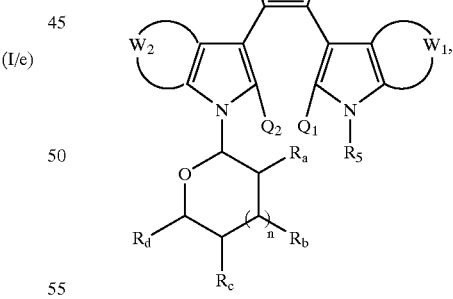

(I/g)

wherein X, Y, $X_1$, $Y_1$, $W_1$, $W_2$, $R_a$, $R_b$, $R_c$, $R_d$, n, $Q_1$, $Q_2$ and $R_5$ are as defined hereinbefore, which compound of formula (I/g) is then subjected to the action of ammonium hydroxide solution in a protic medium to yield the compounds of formula (I/h), a particular case of the compounds of formula (I):

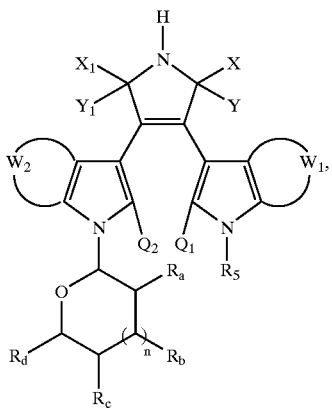

(I/h)

wherein X, Y, $X_1$, $Y_1$, $W_1$, $W_2$, $R_a$, $R_b$, $R_c$, $R_d$, n, $Q_1$, $Q_2$ and $R_5$ are as defined hereinbefore, or, in the particular case where $R_a$ represents a tosyl group and $Q_1$ and $Q_2$, together with the carbon atoms carrying them, form an aromatic bond, is treated with sodium azide to yield the compound of formula (I/i), a particular case of the compounds of formula (I):

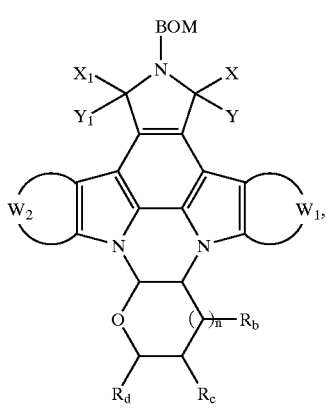

(I/i)

wherein BOM, X, Y, $X_1$, $Y_1$, $W_1$, $W_2$, $R_b$, $R_c$, $R_d$ and n are as defined hereinbefore, which compound of formula (I/i) is treated in like manner to the compounds of formula (I/f) to yield the compound of formula (I/j), a particular case of the compounds of formula (I):

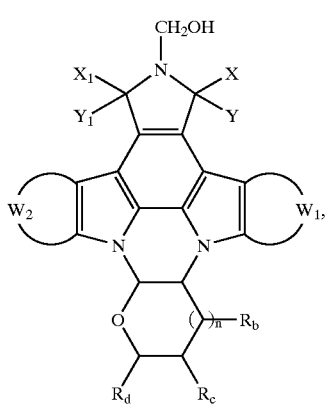

(I/j)

wherein X, Y, $X_1$, $Y_1$, $W_1$, $W_2$, $R_b$, $R_c$, $R_d$ and n are as defined hereinbefore, which compound of formula (I/j) is subjected to the same reaction conditions as the compounds of formula (I/g) to yield the compound of formula (I/k), a particular case of the compounds of formula (I):

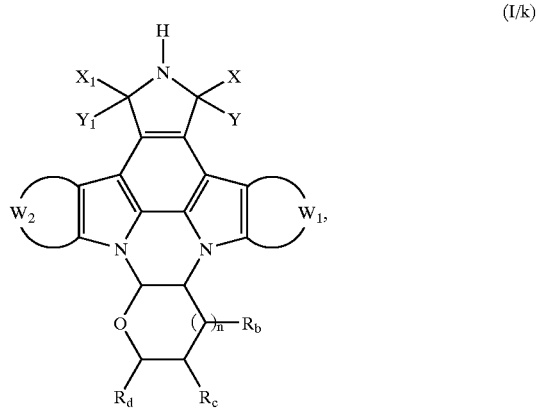

(I/k)

wherein X, Y, $X_1$, $Y_1$, $W_1$, $W_2$, $R_b$, $R_c$, $R_d$ and n are as defined hereinbefore, or, in the particular case where $R_d$ represents a tosyl group and $Q_1$ and $Q_2$, together with the carbon atoms carrying them, form an aromatic bond, is treated with sodium azide to yield the compound of formula (I/l), a particular case of the compounds of formula (I):

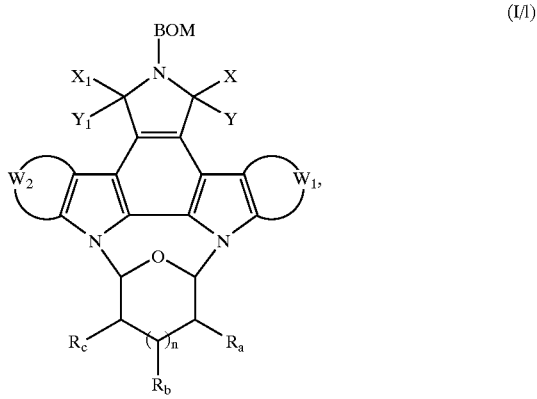

(I/l)

wherein X, Y, $X_1$, $Y_1$, $W_1$, $W_2$, $R_a$, $R_b$, $R_c$ and n are as defined hereinbefore, which compound of formula (I/l) is treated in like manner to the compounds of formula (I/f) to yield the compound of formula (I/m), a particular case of the compounds of formula (I):

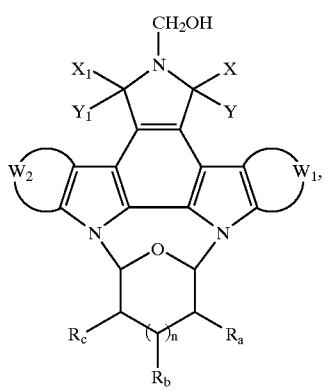

(I/m)

wherein X, Y, $X_1$, $Y_1$, $W_1$, $W_2$, $R_a$, $R_b$, $R_c$ and n are as defined hereinbefore, which compound of formula (I/m) is subjected to the same reaction conditions as the compounds of formula (I/g) to yield the compound of formula (I/n), a particular case of the compounds of formula (I):

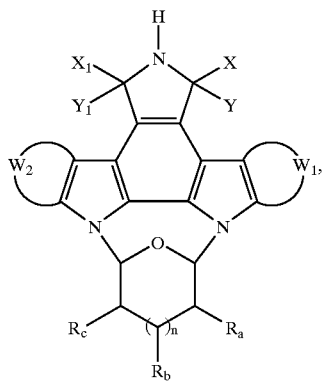

(I/n)

wherein X, Y, $X_1$, $Y_1$, $W_1$, $W_2$, $R_a$, $R_b$, $R_c$ and n are as defined hereinbefore, the totality of the compounds of formulae (I/h), (I/k) and (I/n) forming the compounds of formula (I/o):

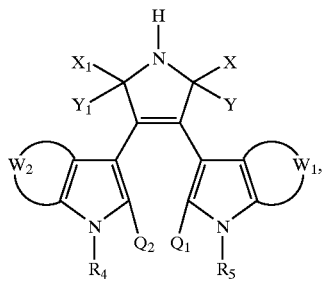

(I/o)

wherein X, Y, $X_1$, $Y_1$, $W_1$, $W_2$, $R_4$, $R_5$, $Q_1$ and $Q_2$ are as defined for formula (I), which compound of formula (I/o) is treated with aqueous sodium hydroxide solution and is then placed in the presence of hydrochloric acid to yield the compound of formula (IX):

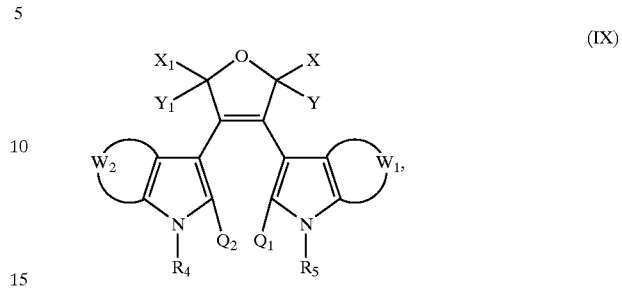

(IX)

wherein X, Y, $X_1$, $Y_1$, $W_1$, $W_2$, $R_4$, $R_5$, $Q_1$ and $Q_2$ are as defined hereinbefore, which compound of formula (IX) is subjected to the action of a compound of formula (X):

$$R_{3a}-NH_2 \qquad (X),$$

wherein $R_{3a}$ is as defined for $R_3$ in formula (I) except for the meaning of a hydrogen atom, to yield the compound of formula (I/p), a particular case of the compounds of formula (I):

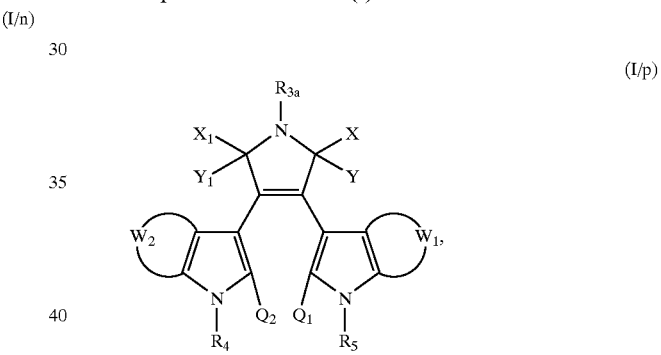

(I/p)

wherein X, Y, $X_1$, $Y_1$, $W_1$, $W_2$, $R_{3a}$, $R_4$, $R_5$, $Q_1$ and $Q_2$ are as defined hereinbefore, the totality of the compounds of formulae (I/o) and (I/p) forming the compounds of formula (I/q):

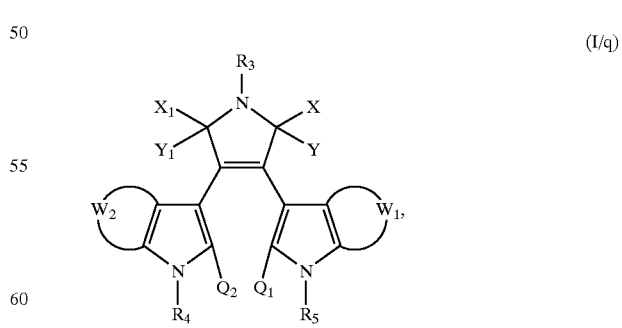

(I/q)

wherein X, Y, $X_1$, $Y_1$, $W_1$, $W_2$, $R_3$, $R_4$, $R_5$, $Q_1$ and $Q_2$ are as defined for formula (I), which compound of formula (I/q) is subjected to a reaction of aromatic electrophilic addition or of aromatic nucleophilic addition, according to customary conditions of organic synthesis well known to the person skilled in the art, to yield the compound of formula (I/r), a particular case of the compounds of formula (I):

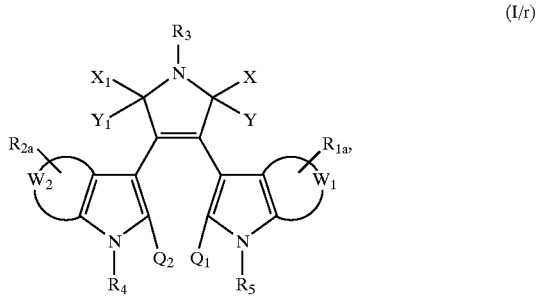

(I/r)

wherein X, Y, $X_1$, $Y_1$, $W_1$, $W_2$, $R_3$, $R_4$, $R_5$, $Q_1$ and $Q_2$ are as defined hereinbefore, and $R_{1a}$ and $R_{2a}$ are as defined for $R_1$ and $R_2$, respectively, except that $R_{1a}$ and $R_2$a cannot simultaneously represent hydrogen atoms, the compounds of formulae (I/a) to (I/r) constituting the totality of the compounds of formula (I), which are purified, if necessary, according to conventional purification techniques, which may be, if desired, separated into their different isomers according to a conventional separation technique, whose substituents $R_a$, $R_b$, $R_c$ and $R_d$ are modified according to conventional methods of organic synthesis used in the area of sugar chemistry, and which are converted, if desired, into their addition salts with a pharmaceutically acceptable acid or base.

The compounds of formulae (II), (III), (VI), ($a_1$), (VIII) and (X) either are commercially available compounds or are obtained according to conventional methods of organic synthesis that are readily accessible to the person skilled in the art.

The compound of formula (IX) is useful as a synthesis intermediate in obtaining compounds of formula (I).

The compounds of formula (I) have especially valuable anti-tumour properties. The characteristic properties of these compounds allow them to be used therapeutically as anti-tumour agents.

The present invention relates also to pharmaceutical compositions comprising, as active ingredient, at least one compound of formula (I), an optical isomer thereof, or an addition salt thereof with a pharmaceutically acceptable acid or base, alone or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, soft gelatin capsules, hard gelatin capsules, suppositories, creams, ointments, dermal gels, injectable or drinkable preparations, aerosols, eye or nose drops etc.

By virtue of the characteristic pharmacological properties of the compounds of formula (I), the pharmaceutical compositions comprising the said compounds of formula (I) as active ingredient are accordingly especially useful in the treatment of cancers.

The useful dosage varies according to the age and weight of the patient, the route of administration, the nature and severity of the disorder and the administration of any associated treatments, and ranges from 1 mg to 500 mg per day in one or more administrations.

The Examples which follow illustrate the invention but do not limit it in any way. The starting materials used are materials that are known or that are prepared according to known procedures.

The structures of the compounds described in the Examples have been determined according to customary spectrophotometric techniques (infrared, nuclear magnetic resonance, mass spectrometry . . . ).

Preparation A: 1-[(benzyloxy)methyl]-3-[1-(phenylsulphonyl)-1H-indol-3-yl]-4-(1H-pyrrolo[2,3-b]pyrid-3-yl)-1H-pyrrole-2,5-dione Step A: 1-[(benzyloxy)methyl]-3-bromo-4-(1H-indol-3-yl)-1H-pyrrole-2,5-dione A solution of ethylmagnesium bromide is prepared, starting from magnesium (6.75 mmol) suspended in bromoethane (6.75 mmol) and dry tetrahydrofuran (5 ml). The solution is stirred at ambient temperature for 15 minutes and is then heated at 40° C. for 20 minutes. A solution of indole (6.75 mmol) in 40 ml of dry tetrahydrofuran is then added dropwise. After stirring for 1 hour at 40° C., the reaction mixture is cooled and then a solution of N-benzyloxymethyl-2,3-dibromomaleimide (3.38 mmol) in 40 ml of dry tetrahydrofuran is added dropwise. The reaction mixture is stirred for 15 hours and is then hydrolysed with saturated aqueous ammonium chloride solution. The organic product is extracted with ethyl acetate, and the organic phases are then combined, dried over magnesium sulphate and filtered. After evaporating off the solvent and purifng the residue by chromatography on silica gel (cyclohexane/ethyl acetate: 4/1), the expected product is isolated.

Melting point=115–117° C.

Step B: 1-[(benzyloxy)methyl]-3-bromo-4-[1-(phenylsulphonyl)-1H-indol-3-yl]-1H-pyrrole-2,5-dione To a suspension, cooled to 0° C., of sodium hydride (5.45 mmol) in 10 ml of dry tetrahydrofuran, there is added, dropwise, a solution of the compound of Step A (2.53 mmol) in 20 ml of tetrahydrofuran. After stirring for 1 hour at 0° C., benzenesulphonyl chloride (4.04 mmol) is added dropwise. The reaction mixture is then stirred for 4 hours at ambient temperature and is then hydrolysed with saturated aqueous ammonium chloride solution. The organic product is extracted with ethyl acetate, and the organic phases are then combined, washed with saturated aqueous sodium chloride solution, dried over magnesium sulphate and filtered. After evaporating off the solvent and purifying the residue by chromatography on silica gel (cyclohexane/ethyl acetate: 85/15), the expected product is isolated.

Melting point=49–51° C.

Step C: 1-[(benzyloxy)methyl]-3-[1-(phenylsulphonyl)-1H-indol-3-yl]-4-(1H-pyrrolo[2, 3-b]pyrid-3-yl)-1H-pyrrole-2, 5-dione To a solution, held at −15° C., of 7-azaindole (1.542 mmol), dissolved in 10 ml of dry toluene, there is added, dropwise, a 1M solution of LiHMDS in hexane (1.78 mmol). After stirring for 1 hour at −15° C., a solution of the compound of Step B (0.637 mmol), dissolved in 10 ml of dry toluene, is added, dropwise, at −20° C. After 24 hours at ambient temperature, the reaction mixture is hydrolysed with saturated aqueous ammonium chloride solution and the pH is then adjusted to 7. The mixture is extracted with ethyl acetate. The organic phases are combined, washed with saturated aqueous sodium chloride solution, dried over magnesium sulphate and filtered. After purifying by chromatography on silica gel (cyclohexane/ethyl acetate: 3/2), the expected product is isolated.

Melting point=94–96° C.

Preparation B: 1-[(benzyloxy)methyl]-3-(1H-indol-3-yl)-4-[1-(phenylsulphonyl)-1H-pyrrolo[2,3-b]-pyrid-3-yl]-1H-pyrrole-2,5-dione Step A: 1-[(benzyloxy)methyl]-3-bromo-4-(1H-pyrrolo[2,3-b]pyrid-3-yl)-1H-pyrrole-2,5-dione A solution of ethylmagnesium bromide is prepared, starting from magnesium (6.00 mmol) suspended in bromoethane (6.00 mmol) and dry tetrahydrofuran (2.5 ml). The solution is stirred at ambient temperature for 1 hour and then 7-azaindole (6.00 mmol), dissolved in 20 ml of anhydrous toluene, is added dropwise. After stirring at ambient temperature for 1 hour 30 minutes, a solution of N-benzyloxymethyl-2,3-dibromomaleimide (2.01 mmol) in 20 ml of anhydrous toluene is added dropwise. After 20 minutes, 30 ml of dry dichloromethane are added; the reaction mixture is then stirred at 40° C. for 65 hours and hydrolysed with saturated aqueous ammonium chloride solution. The organic product is extracted with ethyl acetate, and the organic phases are then combined, dried over magnesium sulphate and filtered. After evaporating off the solvent and purifying the residue by chromatography on silica gel (cyclohexane/ethyl acetate: 3/2, and then toluene/ethyl acetate: 7/3), the expected product is isolated.

Melting point=168–170° C.

Step B: 1-[(benzyloxy)methyl]-3-bromo-4-[1-(phenylsulphonyl)-1H-pyrrolo[2,3-b]-pyrid-3-yl]-1H-pyrrole-2,5-dione The product is obtained according to the procedure of Step B of Preparation A, using the product obtained in Step A above as substrate.

Melting point=123–125° C.

Step C: 1-[(benzyloxy)methyl]-3-(1H-indol-3-yl)-4-[1-(phenylsulphonyl)-1H-pyrrolo-[2,3-b]pyrid-3-yl]-1H-pyrrole-2,5-dione A solution of ethylmagnesium bromide is prepared, starting from magnesium (0.62 mmol) suspended in bromoethane (0.62 mmol) and dry tetrahydrofuran (0.4 ml). The solution is stirred at ambient temperature for 15 minutes and is then heated at 40° C. for 20 minutes. A solution of indole (0.65 mmol) in 3 ml of anhydrous toluene is then added dropwise. After stirring for 1 hour at 40° C., the reaction mixture is cooled and then a solution of the compound obtained in Step B (0.254 mmol) in 5 ml of anhydrous toluene is added dropwise. The reaction mixture is stirred for 15 hours and is then hydrolysed with saturated aqueous ammonium chloride solution. The organic product is extracted with ethyl acetate, and the organic phases are then combined, dried over magnesium sulphate and filtered. After evaporating off the solvent and purifying the residue by chromatography on silica gel (cyclohexane/ethyl acetate: 3/2), the expected product is isolated.

Melting point=86–88° C.

Preparation C: 1-[(benzyloxy)methyl]-3-[1-(phenylsulphonyl)-1H-pyrrolo[2,3-b]-pyrid-3-yl]4-(1H-pyrrolo[2,3-b]pyrid-3-yl)-1H-pyrrole-2,5-dione The product is obtained according to the procedure of Step C of Preparation A, using the compound obtained in Step B of Preparation B as substrate.

Melting point=115–117° C.

Preparation D: 1-methyl-3-[1-(phenylsulphonyl)-1H-pyrrolo[2,3-b]pyrid-3-yl]-4-(1H-pyrrolo[2,3-b]pyrid-3-yl)-1H-pyrrole-2,5-dione Step A: 3-bromo-1-methyl-4-(1H-pyrrolo[2,3-b]pyrid-3-yl)-1H-pyrrole-2,5-dione A solution of ethylmagnesium bromide is prepared, starting from magnesium (12.7 mmol) suspended in bromoethane (12.7 mmol) and dry tetrahydrofuran (5 ml). The solution is stirred at ambient temperature for 1 hour and then 7-azaindole (12.7 mmol), dissolved in 40 ml of anhydrous toluene, is added dropwise. After stirring at ambient temperature for 1 hour 30 minutes, a solution of N-methyl-2,3-dibromomaleimide (3.53 mmol) in 40 ml of anhydrous toluene is added dropwise. After 20 minutes, 60 ml of dry dichloromethane are added; the reaction mixture is then stirred at 40° C. for 75 hours and hydrolysed with saturated aqueous ammonium chloride solution. The organic product is extracted with ethyl acetate, and the organic phases are then combined, dried over magnesium sulphate and filtered. After evaporating off the solvent and purifying the residue by chromatography on silica gel (cyclohexane/ethyl acetate: 3/2), the expected product is isolated.

Melting point=158° C.

Step B: 3-bromo-1-methyl-4-[1-(phenylsulphonyl)-1H-pyrrolo[2,3-b]pyrid-3-yl]-1H-pyrrole-2,5-dione To a suspension, cooled to 0° C., of sodium hydride (4.00 mmol) in 10 ml of dry tetrahydrofuran, there is added, dropwise, a solution of the compound obtained in Step A (1.89 mmol) in 40 ml of tetrahydrofuran and 5 ml of dimethylformamide. After stirring for 1 hour at 0° C., benzenesulphonyl chloride (3.02 mmol) is added dropwise. The reaction mixture is then stirred for 4 hours at ambient temperature and is then hydrolysed with saturated aqueous ammonium chloride solution. The organic product is extracted with ethyl acetate, and the organic phases are then combined, washed with saturated aqueous sodium chloride solution, dried over magnesium sulphate and filtered. After evaporating off the solvent and purifying the residue by chromatography on silica gel (cyclohexane/ethyl acetate: 4/1), the expected product is isolated.

Melting point=198° C.

Step C: 1-methyl-3-[1-(phenylsulphonyl)-1H-pyrrolo[2,3-b]pyrid-3-yl]-4-(1H-pyrrolo[2,3-b]pyrid-3-yl)-1H-pyrrole-2,5-dione The product is obtained according to the procedure of Step C of Preparation A, using the product obtained in Step B above as substrate.

Melting point=180° C.

Preparation E: tert-butyl 3-[1-methyl-2,5-dioxo4-(1H-pyrrolo[2,3-b]pyrid-3-yl)-2,5-dihydro-1H-pyrrol-3-yl]-1H-indole-1-carboxylate Step A: 3-bromo-4-(1H-indol-3-yl)-1-methyl-1H-pyrrole-2,5-dione A solution containing 1.445 g of indole, dissolved in 29 ml of dry tetrahydrofuran, is held between −20 and −10° C. under argon, and then 26 ml of LiHMDS (1M in hexane) are added, dropwise, over the course of 15 minutes. After 45 minutes at −10° C., the solution is diluted with 15 ml of additional tetrahydrofuran, and a solution containing 2 g of N-methyl-2,3-dibromomaleimide dissolved in 17 ml of tetrahydrofuran is added dropwise over the course of 30 minutes. After 15 minutes at −10° C. and 15 minutes at 0° C., the reaction is stopped by the addition, at 0° C., of 50 ml of 0.3N hydrochloric acid solution. The reaction mixture is extracted with ethyl acetate, and the organic phases are washed with saturated NaCl solution, dried over MgSO$_4$ and then evaporated under reduced pressure. The desired product is precipitated using methanol.

Melting point=167–168° C.

Step B: tert-butyl 3-(4-bromo-1-methyl-2,5-dioxo-2,5-dihydro-1H-pyrrol-3-yl)-1H-indole-1-carboxylate A solution, under an inert atmosphere, containing 1 g of the product obtained in Step A, 30 mg of 4-dimethylaminopyridine, 1.58 g of Boc$_2$O and 15 ml of dry tetrahydrofuran is stirred at ambient temperature for 24 hours. After removal of the solvents under reduced pressure, the crude reaction product is purified by chromatography (petroleum ether/AcOEt/NEt$_3$: 8/2/1%), allowing the expected product to be isolated.

Melting point=137–138° C.

Step C: tert-butyl 3-[1-methyl-2,5-dioxo-4-(1H-pyrrolo[2,3-b]pyrid-3-yl)-2,5-dihydro-1H-pyrrol-3-yl]-1H-indole-1-carboxylate To a solution, maintained at −10° C., of 7-azaindole (1.78 mmol), dissolved in 10 ml of dry toluene, there is added, dropwise, a solution of commercial LiHMDS (1M in hexane) (4.6 mmol). After stirring for 1 hour at −10° C., a solution of the product obtained in Step B (0.85 mmol), dissolved in 10 ml of dry toluene, is added dropwise at ambient temperature. After stirring for 24 hours at ambient temperature, the reaction mixture is hydrolysed with saturated aqueous ammonium chloride solution and the pH is then adjusted to 7. The mixture is extracted with ethyl acetate. The organic phases are combined, washed with aqueous sodium chloride solution and dried over magnesium sulphate. After purification by chromatography on silica gel (cyclohexane/ethyl acetate/triethylamine: 7/3/1%), the expected product is isolated.

Melting point=180° C.

Preparation F: 13-(β-D-glucopyranosyl)-12,13-dihydrofuro[3,4-c]pyrido-[3',2':4,5] pyrrolo [2,3-a]carbazole-5,7-dione Step A: 3-(1H-indol-3-yl)-4-[1-(β-D-glucopyranosyl)-1H-pyrrolo[2,3-b]pyrid-3-yl]-1H-furan-2,3-dione To a suspension of the compound of Example 16b (0.488 mmol) in 40 ml of water there are added sodium hydroxide (7 mmol) and 30 ml of tetrahydrofuran. The reaction mixture is stirred for 1 hour 30 minutes at ambient temperature and is then acidified to pH=1 using 2N hydrochloric acid solution and stirred for a further 30 minutes. The reaction mixture is taken up in a water/ethyl acetate mixture, and the organic product is extracted with ethyl acetate. The organic phases are combined, dried over magnesium sulphate and filtered, and the solvent is evaporated off. The product is purified by chromatography on silica gel (ethyl acetate/methanol: 95/5), allowing the expected product to be isolated.

Melting point=182–183° C. Infra-red (KBr), $v_{C=O}$=1755, 1820 cm$^{-1}$; $v_{NH}$=3000–3600 cm$^{-1}$.

Step B: 13-(β-D-glucopyranosyl)-12,13-dihydrofuro[3,4-c]pyrido[3',2':4,5]pyrrolo-[2,3-a]carbazole-5,7-dione The product is obtained according to the procedure of Example 1c, using the compound of Step A above as substrate.

Melting point:>300° C. Infra-red (KBr), $v_{C=O}$=1755, 1825 cm$^{-1}$; $v_{NH}$=3200–3600 cm$^{-1}$.

Preparation G: 1-methyl-3-(1H-indol-3-yl)-4-[1-(phenylsulphonyl)-1H-pyrrolo-[2,3-b]pyrid-3-yl]-1H-pyrrole-2,5-dione The product is obtained according to the procedure of Step C of Preparation B, using the product obtained in Step B of Preparation D as substrate.

Preparation H: tert-butyl 3-[1-methyl-2,5-dioxo-4-(1H-pyrrolo[3,2-c]pyrid-3-yl)-2,5-dihydro-1H-pyrrolo-3-yl]-1H-indole-1-carboxylate To a solution, maintained at ambient temperature, of 5-azaindole (7.89 mmol), dissolved in 15 ml of dry toluene, there is added, dropwise, a solution of LiHMDS (1M in hexane) (6.25 mmol). After stirring for 1 hour 15 minutes at ambient temperature, a solution of the product obtained in Step B of Preparation E (3.77 mmol), dissolved in 10 ml of toluene and 15 ml of dichloromethane, is added at ambient temperature. After stirring for 12 hours at ambient temperature, the mixture is extracted with ethyl acetate. The organic phases are combined, dried over magnesium sulphate and filtered. After purification by chromatography on silica gel (petroleum ether/ethyl acetate/triethylamine: 1/1/1% and then ethyl acetate/triethylamine: 9/1), the expected product is isolated.

Melting point: 218° C. decomposition Infra-red (KBr), $v_{C=O}$=1703, 1735 cm$^{-1}$; $v_{NH}$=3200–3300 cm$^1$.

EXAMPLE 1a

1-[(benzyloxy)methyl]-3-[1-(2,3,4,6-tetra-O-acetyl-β-D-glucopyranosyl)-1H-pyrrolo[2,3-b]pyrid-3-yl]-4-[1-(phenylsulphonyl)-1H-indol-3-yl]-1H-pyrrole-2,5-dione To a solution of the compound of Preparation A (0.927 mmol), dissolved in 40 ml of dry tetrahydrofuran, there are added 2,3,4,6-tetra-O-acetylglucopyranose (1.95 mmol) and triphenylphosphine (1.95 mmol). The reaction mixture is cooled to −78° C., and then DEAD (1.95 mmol) is added dropwise. The temperature is slowly raised to ambient temperature, and the reaction mixture is then stirred for a further 15 hours. After hydrolysis, the organic product is extracted with ethyl acetate. The organic phases are combined, dried over magnesium sulphate and filtered, and the solvent is evaporated off. After purification by chromatography on silica gel (cyclohexane/ethyl acetate: 65/35, and then toluene/ethyl acetate 3/2), the β-glycosylated compound is obtained in the form of yellow crystals and the α-glycosylated compound is obtained in admixture with triphenylphosphine oxide.

Melting point=105–107° C. (β-glycosylated compound).

EXAMPLE 1b

1-[(benzyloxy)methyl]-3-(1H-indol-3-yl)-4-[1-(2,3,4,6-tetra-O-acetyl-β-D-glucopyranosyl)-1H-pyrrolo[2,3-b]pyrid-3-yl]-1H-pyrrole-2,5-dione To a solution of the β-glycosylated compound of Example 1a (0.565 mmol), dissolved in 20 ml of dry tetrahydrofuran, there is added a solution of tetrabutylammonium fluoride (1.1M in tetrahydrofuran) (1.86 mmol). The reaction mixture is stirred for 2.30 hours at ambient temperature. After hydrolysis, the organic product is extracted with ethyl acetate. The organic phases are combined, dried over magnesium sulphate and filtered. After evaporating off the solvent, the residue is purified by chromatography on silica gel (cyclohexane/ethyl acetate: 2/3), allowing the expected product to be isolated.

Melting point=117–119° C.

EXAMPLE 1c

6-[(benzyloxy)methyl]-13-(2,3,4,6-tetra-O-acetyl-β-D-gluco-pyranosyl)-12,13-dihydro-5H-pyrido[3',2':4,5]pyrrolo[2,3-a]-pyrrolo[3,4-c]carbazole-5,7(6H)-dione To a solution of the compound of Example 1b (0.409 mmol), dissolved in 500 ml of benzene, there is added iodine (4.90 mmol). The mixture is irradiated in a quartz reactor equipped with an immersible medium-pressure mercury-vapour U.V. lamp of 400 W for 1 hour 30 minutes. The solvent is evaporated off; the crude reaction product is taken up in ethyl acetate and washed with aqueous sodium thiosulphite solution and then with saturated aqueous sodium chloride solution. The organic phase is dried over magnesium sulphate and filtered, and the solvent is evaporated off. After purification by chromatography on silica gel (cyclohexane/ethyl acetate: 3/2), the expected product is isolated.

Melting point=109–111° C. Infra-red (KBr), $v_{C=O}$=1710, 1760 cm$^{-1}$; $v_{NH}$=3300–3500 cm$^{-1}$.

EXAMPLE 2

6-(hydroxymethyl)-13-(2,3,4,6-tetra-O-acetyl-β-D-glucopyranosyl)-12,13-dihydro-5H-pyrido[3',2':4,5]pyrrolo[2,3-a]pyrrolo[3,4-c]-carbazole-5,7(6H)-dione To a solution of the compound of Example 1c (0.067 mmol) in 3 ml of dry methanol and 1 ml of dry ethyl acetate there is added 10% palladium-on-carbon (18.1 mg). The reaction mixture is degassed twice and is then stirred at ambient temperature under a hydrogen atmosphere (1 bar). After 24 hours, more 10% palladium-on-carbon (21.0 mg) is added. The reaction mixture is degassed again and then held under a hydrogen atmosphere for 48 hours. The mixture is filtered over Celite, and the solid is then washed with methanol and ethyl acetate. After evaporating off the solvents and purifying the residue by chromatography on silica gel (cyclohexane/ethyl acetate: 65/35), the expected product is isolated.

Melting point=154–156° C. Infra-red (KBr), $v_{C=O}$=1705, 1760 cm$^{-1}$; $v_{NH}$=3200–3600 cm$^{-1}$.

EXAMPLE 3

13-(β-D-glucopyranosyl)-12,13-dihydro-5H-pyrido[3',2':4,5]pyrrolo-[2,3-a]pyrrolo[3,4-c]carbazole-5,7(6H)-dione To a solution of the compound of Example 2 (0.030 mmol), dissolved in 9.4 ml of methanol, there is added 28% aqueous ammonium hydroxide solution (8 ml). The mixture is stirred for 19 hours at ambient temperature. After evaporating off the solvents, the residue is taken up in a mixture of water/ethyl acetate and is then filtered over a frit. The crystals are successively washed with ethyl acetate and then with methanol. The expected compound is obtained in the form of yellow crystals.

Melting point>300° C. Infra-red (KBr), $v_{C=O}$=1710, 1740 cm$^{-1}$; $v_{NH,OH}$=3100–3600 cm$^{-1}$.

EXAMPLE 4

9-bromo-13-(β-D-glucopyranosyl)-12,13-dihydro-5H-pyrido-[3',2':4,5]pyrrolo[2,3-a]pyrrolo[3,4-c]carbazole-5,7(6H)-dione To a solution, cooled to 0° C., of the compound of Example 3 (0.043 mmol) in 2 ml of tetrahydrofuran there is added, dropwise, a solution of N-bromosuccinimide (0.866 mmol), dissolved in 1.5 ml of tetrahydrofuran. The mixture is stirred for 5 days at ambient temperature, protected from light. After hydrolysis for 15 minutes, saturated aqueous sodium thiosulphite solution is added. The residue is then extracted with ethyl acetate. The organic phase is dried over magnesium sulphate and filtered, and the solvent is evaporated off. The residue obtained is dissolved in 8 ml of methanol, and then 28% aqueous ammonium hydroxide solution (9 ml) is added. The mixture is stirred for 22 hours at ambient temperature, protected from light. After evaporating off the solvents, the residue is taken up in a water/ethyl acetate mixture and is then filtered over a frit. The crystals are washed with ethyl acetate, allowing the expected product to be obtained.

Melting point>300° C. Infra-red (KBr), $v_{C=O}$=1710, 1750 cm$^{-1}$; $v_{NH,OH}$=3200–3600 cm$^{-1}$. cl EXAMPLE 5

9-nitro-13-(β-D-glucopyranosyl)-12,13-dihydro-5H-pyrido-[3',2':4,5]pyrrolo[2,3-a]pyrrolo[3,4-c]carbazole-5,7(6H)-dione A solution of Mallinckrodt's ether (13 ml of tetrahydrofuran, 2.1 ml of fuming nitric acid) (14 ml), at 0° C., is added dropwise to the compound of Example 3 (0.061 mmol), cooled to 0° C. After 10 minutes, the mixture is raised to ambient temperature and is stirred for 21 hours. After hydrolysis, the organic product is extracted with ethyl acetate. The organic phases are combined, dried over magnesium sulphate and filtered, and the solvent is evaporated off. The residue is dissolved in 10 ml of methanol, and then 28% aqueous ammonium hydroxide solution (17 ml) is added dropwise. The mixture is stirred for 16 hours at ambient temperature. After evaporating off the solvents, the residue is taken up in a water/ethyl acetate mixture and is then filtered over a frit. The crystals are washed with ethyl acetate, allowing the expected product to be isolated.

Melting point>300° C. Infra-red (KBr), $v_{C=O}$=1710, 1760 cm$^{-1}$; $v_{NH,OH}$=3300–3600 cm$^{-1}$.

EXAMPLE 6a

1-[(benzyloxy)methyl]-3-(1H-indol-3-yl)-4-[1-(2,3,4,6-tetra-O-acetyl-α-D-glucopyranosyl)-1H-pyrrolo[2,3-b]pyrid-3-yl]-1H-pyrrole-2,5-dione To a solution of the α-glycosylated compound of Example 1a (0.034 mmol) in 3 ml of dry tetrahydrofuran there is added a solution of tetrabutylammonium fluoride (1.1M in tetrahydrofuran) (0.132 mmol). The reaction mixture is stirred for 2.30 hours at ambient temperature. After hydrolysis, the organic product is extracted with ethyl acetate. The organic phases are combined, dried over magnesium sulphate and filtered. After evaporating off the solvent, the residue is purified by chromatography on silica gel (cyclohexane/ethyl acetate: 2/3), allowing the expected product to be obtained.

EXAMPLE 6b

6-[(benzyloxy)methyl]-13-(2,3,4,6-tetra-O-acetyl-α-D-glucopyranosyl)-12,13-dihydro-5H-pyrido[3',2':4,5]pyrrolo[2,3-a]-pyrrolo[3,4-c]carbazole-5,7(6H)-dione The product is obtained according to the procedure of Example 1c.

EXAMPLE 7a

1-[(benzyloxy)methyl]-3-[1-(2,3,4,6-tetra-O-acetyl-β-D-glucopyranosyl)-1H-indol-3-yl]-4-[1-(phenylsulphonyl)-1H-pyrrolo[2,3-b]pyrid-3-yl]-1H-pyrrole-2,5-dione The products are obtained, after chromatography on silica gel according to the procedure of Example 1a, using the compound of Preparation B as substrate.

Melting point=80–82° C. (β-glycosylated compound). Infra-red (KBr), $v_{C=O}$=1710, 1760 cm$^{-1}$.

EXAMPLE 7b

1-[(benzyloxy)methyl]-3-[1-(2,3,4,6-tetra-O-acetyl-β-D-glucopyranosyl)-1H-indol-3-yl]-4-(1H-pyrrolo[2,3-b]pyrid-3-yl)-1H-pyrrole-2,5-dione The product is obtained according to the procedure of Example 1b, using the compound of Example 7a as substrate.

Melting point=115–117° C. Infra-red (KBr), vC=O=1700, 1760 cm$^{-1}$; $v_{NH}$=3100–3600 cm$^{-1}$.

EXAMPLE 7c

6-[(benzyloxy)methyl]-12-(2,3,4,6-tetra-O-acetyl-β-D-glucopyranosyl)-12,13-dihydro-5H-pyrido[3',2':4,5]pyrrolo[2,3-a]-pyrrolo[3,4-c]carbazole-5,7(6,H)-dione The product is obtained according to the procedure of Example 1c, using the compound of Example 7b as substrate.

Melting point=166–168° C. Infra-red (KBr), $v_{C=O}$=1710, 1760 cm$^{-1}$; $v_{NH}$=3360–3420 cm$^{-1}$.

EXAMPLE 8

6-(hydroxymethyl)-12-(2,3,4,6-tetra-O-acetyl-β-D-glucopyranosyl)-12,13-dihydro-5H-pyrido[3',2':4,5]pyrrolo[2,3-a]pyrrolo[3,4-c]-carbazole-5,7(6H)-dione To a solution of the compound of Example 7c (0.090 mmol) in 40 ml of dry methanol and 20 ml of dry ethyl acetate there is added 10% palladium-on-carbon (60 mg). The reaction mixture is degassed twice and is then stirred at ambient temperature under a hydrogen atmosphere (1 bar). After 17 hours, more 10% palladium-on-carbon (31 mg) is added. The reaction mixture is degassed again and is then held under a hydrogen atmosphere for 21 hours. The mixture is filtered over Celite, and the solid is then washed with methanol and with chloroform. After evaporating off the solvents and purifying the residue by chromatography on silica gel (cyclohexane/ethyl acetate: 1/1), the expected product is isolated.

Melting point=264–266° C. Infra-red (KBr), $v_{C=O}$=1710, 1760 cm$^{-1}$; $v_{NH}$=3300–3600 cm$^{-1}$.

EXAMPLE 9

12-(β-D-glucopyranosyl)-12,13-dihydro-5H-pyrido[3',2':4,5]pyrrolo-[2,3-a]pyrrolo[3,4-c]carbazole-5,7(6H)-dione To a solution of the compound of Example 8 (0.040 mmol), dissolved in 13 ml of methanol, there is added 28% aqueous ammonium hydroxide solution (9 ml). The mixture is stirred for 15 hours at ambient temperature. After evaporating off the solvents, the residue is taken up in a water/ethyl acetate mixture and is then filtered over a frit. The crystals are successively washed with ethyl acetate and then with methanol, allowing the expected product to be isolated.

Melting point>250° C., decomposition. Infra-red (KBr), $v_{C=O}$=1720, 1760 cm$^{-1}$; $v_{NH,OH}$=3100–3600 cm$^{-1}$.

EXAMPLE 10a

1-[(benzyloxy)methyl]-3-[1-(2,3,4,6-tetra-O-acetyl-β-D-glucopyranosyl)-1H-pyrrolo[2,3-b]pyrid-3-yl]-4-[1-(phenylsulphonyl)-1H-pyrrolo[2,3-b]pyrid-3-yl]-1H-pyrrole-2,5-dione The products are obtained, after separation on silica gel, according to the procedure of Example 1a, using the compound of Preparation C as substrate.

Melting point=108–110° C. (β-glycosylated compound). Infra-red (KBr), $v_{C=O}$=1720, 1760 cm$^{-1}$.

EXAMPLE 10b

1-[(benzyloxy)methyl]-3-[1-(2,3,4,6-tetra-O-acetyl-β-D-glucopyranosyl)-1H-pyrrolo [2,3-b]pyrid-3-yl]-4-(1H-pyrrolo-[2,3-b]pyrid-3-yl)-1H-pyrrole-2,5-dione The product is obtained according to the procedure of Example 1b, using the compound of Example 10a as substrate.

Melting point=127–129° C. Infra-red (KBr), $v_{C=O}$=1710, 1750 cm$^{-1}$; $v_{NH}$=3300–3500 cm$^{-1}$.

EXAMPLE 10c

6-[(benzyloxy)methyl]-12-(2,3,4,6-tetra-O-acetyl-β-D-glucopyranosyl)-12,13-dihydro-5H-pyrido[2,3-b]pyrido-[3',2':4,5]pyrrolo[3,2-g]pyrrolo[3,4-e]indole-5,7(6H)-dione The product is obtained according to the procedure of Example 1c, using the compound of Example 10b as substrate.

Melting point=194–196° C. Infra-red (KBr), $v_{C=O}$=1690, 1730 cm$^{-1}$; $v_{NH}$=3300–3400 cm$^{-1}$.

EXAMPLE 11

6-(hydroxymethyl)-12-(2,3,4,6-tetra-O-acetyl-β-D-glucopyranosyl)-12,13-dihydro-5H-pyrido[2,3-b]pyrido[3',2':4,5]pyrrolo[3,2-g]-pyrrolo[3,4-e]indole-5,7(6H)-dione To a solution of the compound of Example 10c (0.090 mmol) in 4.5 ml of dry methanol and 1.5 ml of dry ethyl acetate there is added 10% palladium-on-carbon (84.0 mg). The reaction mixture is degassed twice and is then stirred at ambient temperature under a hydrogen atmosphere (1 bar) for 24 hours. After 24 hours, more 10% palladium-on-carbon (42.0 mg) is added. The reaction mixture is degassed again and is then held under a hydrogen atmosphere for 24 hours. The mixture is filtered over Celite, and the solid is washed with methanol and with chloroform. After evaporating off the solvents and purifying the residue by chromatography on silica gel (cyclohexane/ethyl acetate: 3/2), the expected product is isolated.

Melting point>300° C. Infra-red (KBr), $v_{C=O}$=1710, 1760 cm$^{-1}$; $v_{NH}$=3300–3600 cm$^{-1}$.

EXAMPLE 12

12-(β-D-glucopyranosyl)-12,13-dihydro-5H-pyrido[2,3-b]-pyrido[3',2':4,5]pyrrolo[3,2-g]pyrrolo[3,4-e]indole-5,7(6H)-dione To a solution of the compound of Example 11 (0.053 mmol), dissolved in 15 ml of methanol, there is added 28% aqueous ammonium hydroxide solution (13 ml). The mixture is stirred at 40° C. for 21 hours. After evaporating off the solvents, the residue is taken up in a water/ethyl acetate mixture and is then filtered over a frit. The crystals are successively washed with ethyl acetate and then with methanol, allowing the expected product to be isolated.

Melting point>300° C. Infra-red (KBr), $v_{C=O}$=1710, 1760 cm$^{-1}$; $v_{NH,OH}$=3200–3600 cm$^{-1}$.

EXAMPLE 13

6-[(benzyloxy)methyl]-12-(β-D-glucopyranosyl)-12,13-dihydro-5H-pyrido[2,3-b]pyrido[3',2':4,5]pyrrolo[3,2-g]pyrrolo[3,4-e]indole-5,7(6H)-dione To a solution of the compound of Example 10c (0.054 mmol), dissolved in 13 ml of methanol, there is added 28% aqueous ammonium hydroxide solution (13 ml). The mixture is stirred at 40° C. for 19 hours. After evaporating off the solvents, the residue is taken up in a water/ethyl acetate mixture and is then filtered over a frit. The crystals are successively washed with ethyl acetate and then with methanol, allowing the expected product to be isolated.

Melting point>300° C. Infra-red (KBr), $v_{C=O}$=1700, 1750 cm$^{-1}$; $v_{NH,OH}$=3300–3600 cm$^{-1}$.

EXAMPLE 14a

3-[1-(2,3,4,6-tetra-O-acetyl-β-D-glucopyranosyl)-1H-pyrrolo[2,3-b]-pyrid-3-yl]-1-methyl-4-[1-(phenylsulphonyl)-1H-pyrrolo[2,3-b]-pyrid-3-yl]-1H-pyrrole-2,5-dione The product is obtained, after chromatography on silica gel, according to the procedure of Example 1a, using the compound of Preparation D as substrate.

Melting point=116–118° C. (β-glycosylated compound).

EXAMPLE 14b

3-[1-(2,3,4,6-tetra-O-acetyl-β-D-glucopyranosyl)-1H-pyrrolo[2,3-b]-pyrid-3-yl]-1-methyl-4-(1H-pyrrolo[2,3-b]-pyrid-3-yl)-1H-pyrrole-2,5-dione To a solution of the compound of Example 14a (0.046 mmol), dissolved in 4 ml of dry tetrahydrofuran, there is added a solution of tetrabutylammonium fluoride (1.1M in tetrahydrofuran) (0.137 mmol). The reaction mixture is stirred for 2.30 hours at ambient temperature. After hydrolysis, the organic product is extracted with ethyl acetate. The organic phases are combined, dried over magnesium sulphate and filtered. After evaporating off the solvent, the residue is purified by chromatography on silica gel (cyclohexane/ethyl acetate: 3/7), allowing the expected product to be isolated.

Melting point=148–150° C. Infra-red (KBr), $v_{C=O}$=1700, 1760 cm$^{-1}$; $v_{NH}$=3300–3600 cm$^{-1}$.

EXAMPLE 14c 1-methyl-3-[1-(β-D-glucopyranosyl)-1H-pyrrolo[2,3-b]pyrid-3-yl]-4-(1H-pyrrolo[2,3-b]pyrid-3-yl)-1H-pyrrole-2,5-dione To a solution of the compound of Example 14b (0.054 mmol), dissolved in 14 ml of methanol, there is added 28% aqueous ammonium hydroxide solution (10 ml). The reaction mixture is stirred for 26 hours at ambient temperature. After evaporating off the solvents, the residue is purified by chromatography on silica gel (ethyl acetate/methanol: 9/1), allowing the expected product to be isolated.

Melting point=195–197° C. Infra-red(KBr), $v_{C=O}$=1700, 1710 cm$^{-1}$; $v_{NH}$=3200–3600 cm$^{-1}$.

EXAMPLE 14d 6-methyl-12-(2,3,4,6-tetra-O-acetyl-β-D-glucopyranosyl)-12,13-dihydro-5H-pyrido[2,3-b]pyrido[3',2':4,5]pyrrolo[3,2-g]pyrrolo[3,4-e]-indole-5,7(6H)-dione The product is obtained according to the procedure of Example 1c, using the compound of Example 14b as substrate.

Melting point>300° C. Infra-red (KBr), $v_{C=O}$=1703, 1757 cm$^{-1}$; $v_{NH}$=3373 cm$^{-1}$.

EXAMPLE 15

6-methyl-12-(β-D-glucopyranosyl)-12,13-dihydro-5H-pyrido[2,3-b]-pyrido[3',21':4,5]pyrrolo[3,2-g]pyrrolo[3,4-e]indole-5,7(6H)-dione To a solution of the compound of Example 14c (0.066 mmol), dissolved in 40 ml of methanol, there is added 28% aqueous ammonium hydroxide solution (28 ml). The mixture is stirred for 26 hours at 55° C. After evaporating off the solvents, the residue is taken up in a water/ethyl acetate mixture and is then filtered over a frit. The crystals are successively washed with ethyl acetate and then with methanol, allowing the expected product to be isolated.

Melting point>300° C. Infra-red (KBr), $v_{C=O}$=1650, 1700 cm$^{-1}$; $v_{NH,OH}$=3200–3600 cm$^{-1}$.

EXAMPLE 16a tert-butyl 3-{4-[1-(2,3,4,6-tetra-O-acetyl-β-D-glucopyranosyl)-1H-pyrrolo[2,3-b]pyrid-3-yl]-1-methyl-2,5-dioxo-2,5-dihydro-1H-pyrrol-3-yl}-1H-indole-1-carboxylate To a solution of the compound of Preparation E (0.491 mmol), dissolved in 15 ml of dry tetrahydrofuran, there are added 2,3,4,6-tetra-O-acetylglucopyranose (1.09 mmol) and triphenylphosphine (1.09 mmol). The reaction mixture is cooled to −78° C., and then DEAD (1.09 mmol) is added dropwise. The temperature is slowly raised to ambient temperature and the reaction mixture is stirred for a further 15 hours. After hydrolysis, the organic product is extracted with ethyl acetate. The organic phases are combined, dried over magnesium sulphate and filtered, and the solvent is evaporated off. After purification by chromatography on silica gel (cyclohexane/ethyl acetate/triethylamine: 4/1/1%), the expected product is isolated.
Melting point=89–91° C.

EXAMPLE 16b 3-(1H-indol-3-yl)-4-[1-(2,3,4,6-tetra-O-acetyl-β-D-glucopyranosyl)-1H-pyrrolo[2,3-b]pyrid-3-yl]-1-methyl-1H-pyrrole-2,5-dione The compound of Example 16a (0.114 mmol) is dissolved in 20 ml of formic acid. After stirring for 24 hours at ambient temperature, the solution is neutralised by adding, dropwise, triethylamine, and then saturated aqueous sodium bicarbonate solution. The mixture is extracted with ethyl acetate. The organic phases are combined, washed with saturated aqueous sodium chloride solution and are then dried over magnesium sulphate and filtered; the solvent is evaporated off. After purification by chromatography on silica gel (cyclohexane/ethyl acetate: 1/1), the expected product is isolated.
Melting point=119–121° C. Infra-red (KBr), $v_{C=O}$=1700, 1752 cm$^{-1}$; $v_{NH}$=3300–3500 cm$^{-1}$.

EXAMPLE 16c 13-(2,3,4,6-tetra-O-acetyl-β-D-glucopyranosyl)-6-methyl-12,13-dihydro-5H-pyrido[3',2':4,5]pyrrolo[2,3-a]pyrrolo [3,4-c]carbazole-5,7(6H)-dione The product is obtained according to the procedure of Example 1c, using the compound of Example 16b as substrate.
Melting point=302–304° C. Infra-red (KBr), $v_{C=O}$=1700, 1750 cm$^{-1}$; $v_{NH}$=3200–3600 cm$^{-1}$.

EXAMPLE 17

13-(β-D-glucopyranosyl)-6-methyl-12,13-dihydro-5H-pyrido-[3',2':4,5]pyrrolo [2,3-a]pyrrolo [3,4-c] carbazole-5,7(6H)-dione To a solution of the compound of Example 16c (0.067 mmol), dissolved in 20 ml of methanol, there is added 28% aqueous ammonium hydroxide solution (31 ml). The mixture is stirred for 22 hours at 65° C. After evaporating off the solvents, the residue is taken up in a water/ethyl acetate mixture and is then filtered over a frit. The crystals are washed with ethyl acetate, allowing the expected product to be isolated.
Melting point>300° C. Infra-red (KBr), $v_{C=O}$=1690, 1750 cm$^{-1}$; $v_{NH,OH}$=3300–3600 cm$^{-1}$.

EXAMPLE 18

13-(2,3,4,6-tetra-O-acetyl-β-D-glucopyranosyl)-9-bromo-6-methyl-12,13-dihydro-5H-pyrido[3',2':4,5] pyrrolo[2,3-a]pyrrolo[3,4-c]-carbazole-5,7(6H)-dione The product is obtained according to the procedure of Example 4, using the compound of Example 16c as substrate.
Melting point=280–282° C. Infra-red (KBr), $v_{C=O}$=1700, 1760 cm$^{-1}$; $v_{NH}$=3360–3400 cm$^{-1}$.

EXAMPLE 19

13-(β-D-glucopyranosyl)-9-bromo-6-methyl-12,13-dihydro-5H-pyrido[3',2':4,5]pyrrolo[2,3-a]pyrrolo[3,4-c]carbazole-5,7(6H)-dione The product is obtained according to the procedure of Example 4, using the compound of Example 17 as substrate.
Melting point>300° C. Infra-red (KBr), $v_{C=O}$=1680, 1760 cm$^{-1}$; $v_{NH,OH}$=3300–3600 cm$^{-1}$.

EXAMPLE 20

12,13-(β-D-mannopyranosyl)-5H-pyrido[2,3-b]pyrido-[3',2':4,5]pyrrolo[3,2-g]pyrrolo[3,4-e]indole-5,7 (6H)-dione Step 1: 12-(2-O-tosyl-β-D-glucopyranosyl)-12,13-dihydro-5H-pyrido[2,3-b]-pyrido[3'2':4,5]pyrrolo[3,2-g]pyrrolo[3,4-e]indole-5,7(6H)-dione To a solution of the compound of Example 12 (0.17 mmol) in 10 ml of tetrahydrofuran there are added 23.5 mg of potassium carbonate and 1.7 mmol of para-toluenesulphonic acid chloride. The mixture is heated at reflux for 48 hours. After evaporating off the solvent, the residue is taken up in a water/ethyl acetate mixture and is then filtered over a frit. The crystals are successively washed with ethyl acetate and then with methanol, allowing the expected product to be isolated.

Step 2: 12,13-(β-D-mannopyranosyl)-5H-pyrido[2,3-b]pyrido[3',2:4',5]-pyrrolo[3,2-g]pyrrolo[3,4-e]indole-5,7(6H)-dione To a solution of the compound obtained in Step 1 (0.062 mmol) in 1.6 ml of dimethylformamide there is added 0.62 mmol of sodium azide. The mixture is stirred at 70° C. for 6 days and is then cooled, poured into water and extracted with ethyl acetate. The organic phase is washed with saturated NaHCO$_3$ solution and then with saturated NaCl solution and is dried over magnesium sulphate. The solvent is evaporated off and the residue is recrystallised, allowing the expected product to be isolated.

EXAMPLE 21

13-(β-D-glucopyranosyl-6-[2-(diethylamino)ethyl]-12,13-dihydro-5H-pyrido[3',2':4,5]pyrrolo[2,3-a] pyrrolo[3,4-c] carbazole-5,7(6H)-dione hydrochloride To a solution of the compound of Preparation F (0.102 mmol), dissolved in 6 ml of THF, there is added, dropwise, N,N-diethylethylenediamine (0.153 mmol). The mixture is heated at reflux for 5 days, protected from light, and is then cooled and taken up in 1N aqueous hydrochloric acid solution (40 mL). The organic product is extracted with ethyl acetate. The aqueous phases are collected and the pH is adjusted to 12 by adding saturated sodium bicarbonate solution. The organic product is extracted with ethyl acetate. The organic phases are combined, dried over magnesium sulphate and filtered, and the solvent is evaporated off. To a solution, cooled to 0° C., of the resulting amine, dissolved in 500 μl of methanol, there is added, dropwise, 1N aqueous hydrochloric acid solution (200 μl). The mixture is stirred for 30 minutes. The solvent is evaporated off, allowing the expected product to be isolated.

Melting point:>300° C.

EXAMPLE 22a 1-methyl-3-[1-(2,3,4,6-tetra-O-acetyl-β-D-glucopyranosyl)-1H-indol-3-yl]4-[1-(phenylsulphonyl)-1H-pyrrolo[2,3-b]pyrid-3-yl]-1H-pyrrole-2,5-dione The product is obtained according to the procedure of Example 1a, using the compound of Preparation G as substrate.

EXAMPLE 22b 1-methyl-3-[1-(2,3,4,6-tetra-O-acetyl-β-D-glucopyranosyl)-1H-indol-3-yl]4-(1H-pyrrolo[2,3-b]pyrid-3-yl)-1H-pyrrole-2,5-dione The product is obtained according to the procedure of Example 1b using the compound of Example 22a as substrate.

EXAMPLE 22c 6-methyl-12-(2,3,4,6-tetra-O-acetyl-β-D-glucopyranosyl)-12,13-dihydro-5H-pyrido[3',2':4,5]pyrrolo[2,3-a]pyrrolo[3,4-c]carbazole-5,7(6H)-dione The product is obtained according to the procedure of Example 1c, using the compound of Example 22b as substrate.

EXAMPLE 23

6-methyl-12(β-D-glucopyranosyl)-12,13-dihydro-5H-pyrido[3',2':4,5]-pyrrolo[2,3-a]pyrrolo[3,4-c]carbazole-5,7(6H)-dione The product is obtained according to the procedure of Example 15, using the compound of Example 22c as substrate.

EXAMPLE 24a tert-butyl 3-{4-[1-(2,3,4,6-tetra-O-acetyl-β-D-glucopyranosyl)-1H-pyrrolo[3,2-c]pyrid-3-yl)-1-methyl-2,5-dioxo-2,5-dihydro-1H-pyrrol-3-yl]-1H-indole-1-carboxylate The product is obtained according to the procedure of Example 16a, using the compound of Preparation H as substrate.

EXAMPLE 24b 3-(1H-indol-3-yl)-4-[1-(2,3,4,6-tetra-O-acetyl-β-D-glucopyranosyl)-1H-pyrrolo[3,2-c]pyrid-3-yl]-1-methyl-1H-pyrrole-2,5-dione The product is obtained according to the procedure of Example 16b, using the compound of Example 24a as substrate.

EXAMPLE 24c 13-(2,3,4,6-tetra-O-acetyl-β-D-glucopyranosyl)-6-methyl-12,13-dihydro-5H-pyrido[3',4':4,5]pyrrolo[2,3-a]pyrrolo[3,4-c]carbazole-5,7(6H)-dione The product is obtained according to the procedure of Example 16c, using the compound of Example 24b as substrate.

EXAMPLE 25

13-(β-D-glucopyranosyl)-6-methyl-12,13-dihydro-5H-pyrido[3',4':4,5]-pyrrolo[2,3-a]pyrrolo[3,4-c]carbazole-5,7(6H)-dione The product is obtained according to the procedure of Example 17, using the compound of Example 24c as substrate.

EXAMPLE 26c 6-amino-13-(β-D-glucopyranosyl)-12,13-dihydro-5H-pyrido[3',2':4,5]pyrrolo[2,3-a]pyrrolo[3,4-c] carbazole-5,7(6H)-dione A mixture of the compound of Preparation F (0.04 mmol) and hydrazine hydrate (384 μl) is stirred for 24 hours. Water (15 ml) and then a 1N aqueous solution of hydrochloric acid (20 ml) are added. The precipitate is filtered off and then washed with water, allowing the expected product to be isolated.

Melting point>300° C. Infra-red (KBr), $v_{C=O}$=1700, 1750 cm$^{-1}$; $v_{NH,OH}$=3320–3500 cm$^{-1}$.

EXAMPLE 27

13-(6-chloro-6-deoxy-β-D-glucopyranosyl)-6-methyl-12,13-dihydro-5H-pyrido[3',2':4,5]pyrrolo[2,3-a]pyrrolo[3,4-c]carbazole-5,7(6H)-dione To a solution of the compound of Example 17 (0.353 mmol) dissolved in 2.5 ml of pyridine there is added a solution of triphenylphosphine (1.415 mmol) and then carbon tetrachloride (0.707 mmol). The mixture is stirred at ambient temperature for 2.30 hours and is then poured into water. The mixture is extracted with ethyl acetate and the organic phase is washed successively with a 1N aqueous solution of hydrochloric acid, water and a saturated solution of NaHCO$_3$. After evaporating off the solvent and then purifying by chromatography over silica gel (ethyl acetate), the expected product is isolated.

Melting point=275–280° C., decomposition. Infra-red (KBr), $v_{C=O}$=1695, 1750 cm$^{-1}$; $v_{NH,OH}$=3100–3600 cm$^{-1}$.

PHARMACOLOGICAL STUDY OF COMPOUNDS OF THE INVENTION

EXAMPLE 28

In Vitro Activity

Murine Leukaemia L1210

Murine leukaemia L1210 was used in vitro. The cells are cultured in RPMI 1640 complete culture medium containing 10% foetal calf serum, 2 mM glutamine, 50 units/ml of penicillin, 50 μg/ml of streptomycin and 10 mM Hepes, pH: 7.4. The cells are distributed on microplates and exposed to the cytotoxic compounds for 4 doubling periods, or 48 hours. The number of viable cells is then quantified by means of a colorimetric assay, the Microculture Tetrazolium Assay (J. Carmichael et al., Cancer Res., 47, 936–942, (1987)). The results are expressed as IC$_{50}$, the concentration of cytotoxic agent which inhibits the proliferation of the treated cells by 50%. All the compounds of the invention exhibit good cytotoxicity with respect to this cell line. By way of illustration, the compounds of Examples 4, 5, 9 and 12 all have IC$_{50}$ values better than 10$^{-7}$M.

Human Cell Lines

The compounds of the invention were also tested on human cell lines according to the same experimental protocol as that described for murine leukaemia L1210, but with incubation times of 4 days instead of 2 days. By way of example, the compounds of Examples 3, 4, 5, 15, 17 and 19 all have IC$_{50}$ values of less than 1 μM with respect to the following cell lines:neuroblastoma SK-N-MC, epidermoid carcinoma A431 and small cell lung carcinoma H 69.

The various results clearly demonstrate the strong antitumour potential of the compounds of the invention.

EXAMPLE 29

Action on the Cell Cycle

L1210 cells are incubated for 21 hours at 37° C. in the presence of various concentrations of test compounds. The cells are then fixed by 70% (v/v) ethanol, washed twice in PBS and incubated for 30 minutes at 20° C. in PBS that contains 100 μg/ml of RNAse and 50 μg/ml of propidium iodide. The results are expressed in terms of the percentage of the cells that accumulate in the G2+M phase after 21 hours, compared with the control (control: 20%). The compounds of the invention are especially interesting. By way of example, the compounds of Examples 3, 4 and 5, at a concentration of less than 0.5 μM, cause accumulation of at least 80% of cells in the G2+M phase after 21 hours.

EXAMPLE 30

Pharmaceutical Composition:Injectable Solution

| | |
|---|---|
| Compound of Example 3 | 10 mg |
| Distilled water for injectable preparations | 25 ml |

The invention claimed is:
1. A compound selected from those of formula (I):

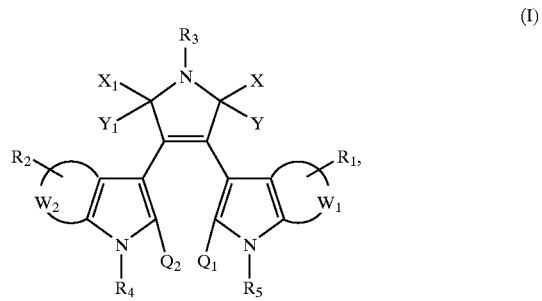

wherein:
$W_1$, $W_2$, together with the carbon atoms to which they are bonded, each represent phenyl or pyridyl, wherein at least one of the groups $W_1$ or $W_2$ represents pyridyl, $R_1$, $R_2$, which may be identical or different, each represents a group of formula U-V, wherein:

U represents a single bond, linear or branched ($C_1$–$C_6$) alkylene chain optionally substituted by one or more identical or different groups selected from halogen and hydroxy, and/or optionally containing one or more unsaturated bonds, V represents a group selected from hydrogen, halogen, cyano, nitro, azido, linear or branched($C_1$–$C_6$)alkyl, aryl, aryl-($C_1$–$C_6$)alkyl in which the alkyl moiety may be linear or branched, hydroxy, linear or branched ($C_1$–$C_6$)alkoxy, aryloxy, aryl-($C_1$–$C_6$) alkoxy in which the alkoxy moiety may be linear or branched, formyl, carboxy, aminocarbonyl, $NR_6R_7$, —C(O)-$T_1$, —C(O)—$NR_6$-$T_1$, —$NR_6$—C(O)-$T_1$, —O—C(O)-$T_1$, —C(O)—O-$T_1$, —O-$T_2$-$NR_6R_7$, —O-$T_2$-$OR_6$, —O-$T_2$-$CO_2R_6$, —$NR_6$-$T_2$-$NR_6R_7$, —$NR_6$-$T_2$-$OR_6$, —$NR_6$-$T_2$-$CO_2R_6$ and —S(O)$_t$-$R_6$, wherein:
$R_6$ and $R_7$, which may be identical or different, each represents a group selected from hydrogen, linear or branched ($C_1$–$C_6$)alkyl aryl, aryl-($C_1$–$C_6$)alkyl groups in which the alkyl moiety may be linear or branched, or $R_6$ and $R_7$, together with the nitrogen atom carrying them, form a saturated, monocyclic or bicyclic heterocycle that has from 5 to 10 ring atoms, and which optionally contains in the ring system a second hetero atom selected from oxygen and nitrogen, and which is optionally substituted by a group selected from linear or branched ($C_1$–$C_6$) alkyl, aryl, aryl-($C_1$–$C_6$)alkyl in which the alkyl moiety may be linear or branched, hydroxy, linear or branched ($C_1$–$C_6$)alkoxy, amino, linear or branched mono-($C_1$–$C_6$)alkylamino, and di-($C_1$–$C_6$)alkylamino in which the alkyl moieties may be linear or branched, $T_1$ represents a group selected from linear or branched ($C_1$–$C_6$)alkyl, aryl, aryl-($C_1$–$C_6$)alkyl in which the alkyl moiety may be linear or branched, linear or branched ($C_1$–$C_6$)alkylene chain substituted by a group selected from —$OR_6$, —$NR_6R_7$, —$CO_2R_6$, —C(O)$R_6$ and —C(O)$NR_6R_7$ wherein $R_6$ and $R_7$ are as defined hereinbefore, and a linear or branched ($C_2$–$C_6$)alkenylene chain substituted by a group selected from —$OR_6$, —$NR_6R_7$, —CO$_2$R$_6$, —C(O)R$_6$ and —C(O)NR$_6$R$_7$ wherein R$_6$ and R$_7$ are as defined hereinbefore, T$_2$ represents linear or branched (C$_1$–C$_6$)alkylene, t represents an integer of from 0 to 2 inclusive, R$_3$ represents a group selected from hydrogen, linear or branched (C$_1$–C$_6$)alkyl, aryl, aryl-(C$_1$–C$_6$)alkyl in which the alkyl moiety may be linear or branched, cycloalkyl, cycloalkyl-(C$_1$–C$_6$)alkyl in which the alkyl moiety may be linear or branched, —OR$_6$, —NR$_6$R$_7$, —O-T$_2$-NR$_6$R$_7$, —NR$_6$-T$_2$-NR$_6$R$_7$, linear or branched (C$_1$–C$_6$)hydroxy-alkylamino, di((C$_1$–C$_6$)hydroxyalkyl) amino in which each alkyl moiety may be linear or branched, —C(O)—R$_6$, —NH—C(O)—R$_6$ and a linear or branched (C$_1$–C$_6$)alkylene chain substituted by one or more identical or different groups selected from halogen, cyano, nitro, —OR$_6$, —NR$_6$R$_7$, —CO$_2$R$_6$, —C(O)R$_6$, linear or branched (C$_1$–C$_6$)hydroxyalkylamino, di((C$_1$–C$_6$)hydroxyalkyl)amino in which the alkyl moieties may be linear or branched, and —C(O)—NHR$_6$, R$_6$, R$_7$ and T$_2$ being as defined hereinbefore, X represents a group selected from hydrogen, hydroxy, linear or branched (C$_1$–C$_6$)alkoxy, mercapto and linear or branched (C$_1$–C$_6$)alkylthio, Y represents hydrogen, or X and Y, together with carbon atom carrying them, form carbonyl or thiocarbonyl, X$_1$ represents a group selected from hydrogen, hydroxy, linear or branched (C$_1$–C$_6$)alkoxy, mercapto and linear or branched (C$_1$–C$_6$)alkylthio, Y$_1$ represents hydrogen, or X$_1$ and Y$_1$, together with carbon atom carrying them, form carbonyl or thiocarbonyl, Q$_1$, Q$_2$ represent hydrogen, or Q$_1$ and Q$_2$, together with carbon atoms carrying them, form an aromatic bond, R$_4$ represents a group of formula (a):

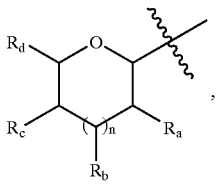

(a)

wherein:

R$_a$, R$_b$ and R$_c$, which may be identical or different, each represent, independently of the others, a group selected from hydrogen, halogen, hydroxy, linear or branched (C$_1$–C$_6$)alkoxy, aryloxy, aryl-(C$_1$–C$_6$) alkoxy in which the alkoxy moiety may be linear or branched, linear or branched (C$_1$–C$_6$)alkyl, aryl-(C$_1$–C$_6$)alkyl in which the alkyl moiety may be linear or branched, aryl, —NR$_6$R$_7$ wherein R$_6$ and R$_7$ are as defined hereinbefore, azido, —N=NR$_6$ (wherein R$_6$ is as defined hereinbefore), —O—C(O)—R$_8$, wherein R$_8$ represents a linear or branched (C$_1$–C$_6$)alkyl (optionally substituted by one or more groups selected from halogen, hydroxy, amino, linear or branched (C$_1$–C$_6$)alkylamino, and di-(C$_1$–C$_6$) alkylamino in which the alkyl moieties may be linear or branched, aryl, aryl-(C$_1$–C$_6$)alkyl in which the alkyl moiety may be linear or branched, cycloalkyl or heterocycloalkyl, R$_d$ represents a methylidene or a group of formula -U$_1$-R$_a$ wherein U$_1$ represents single bond or a methylene and R$_a$ is as defined hereinbefore, n is 0 or 1, R$_5$ represents a group selected from a hydrogen, linear or branched (C$_1$–C$_6$)alkyl, aryl-(C$_1$–C$_6$)alkyl in which the alkyl moiety may be linear or branched, arylsulphonyl, linear or branched (C$_1$–C$_6$)alkyloxycarbonyl, —OR$_6$ and —C(O)—R$_6$ (wherein R$_6$ is as defined hereinbefore), or R$_4$ and R$_5$ together represent, a group of formula (b) or (c):

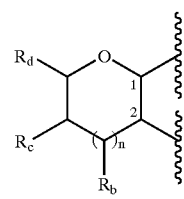

(b)

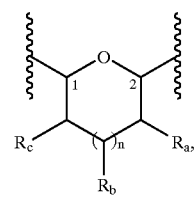

(c)

wherein:

carbon atom 1 is bonded to nitrogen of the ring (A) and carbon atom 2 is bonded to nitrogen of the ring (B), R$_a$, R$_b$, R$_c$ and R$_d$ are as defined hereinbefore, n is 0 or 1, with the proviso that in this case Q$_1$ and Q$_2$ together form an aromatic bond, its enantiomers and diastereoisomers, and addition salts thereof with a pharmaceutically acceptable acid or base, aryl being understood to mean a phenyl, naphthyl, dihydronaphthyl, tetrahydronaphthyl, indenyl or indanyl, each of those groups being optionally substituted by one or more identical or different groups selected from halogen, linear or branched (C$_1$–C$_6$)alkyl, linear or branched (C$_1$–C$_6$)trihaloalkyl, hydroxy, linear or branched (C$_1$–C$_6$)alkoxy, and amino optionally substituted by one or two linear or branched (C$_1$–C$_6$)alkyl.

2. A compound of claim 1, wherein X and Y, together with the carbon carrying them, form carbonyl and X$_1$ and Y$_1$ together with the carbon carrying them, form carbonyl.

3. A compound of claim 1, which is a compound of formula (IA):

4. A compound of claim 1, which is a compound of formula (IB):
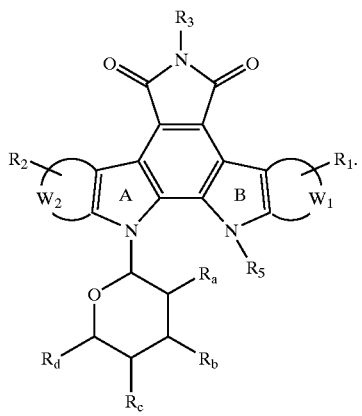
(IA)
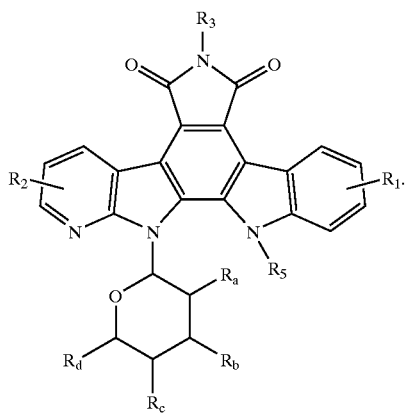
(IB)
5. A compound of claim 1, which is a compound of formula (IC):
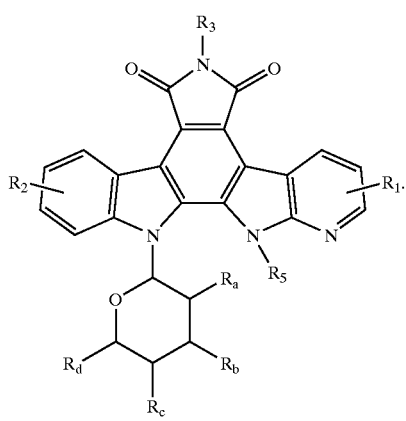
(IC)
6. A compound of claim 1, which is a compound of formula (ID):
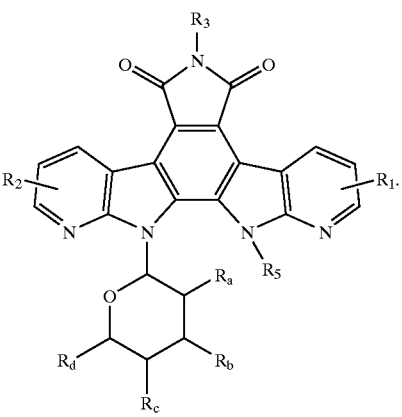
(ID)
7. A compound of claim 1, which is a compound of formula (IE):
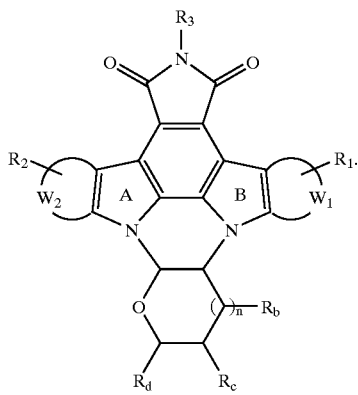
(IE)
8. A compound of claim 1, which is a compound of formula (IF)
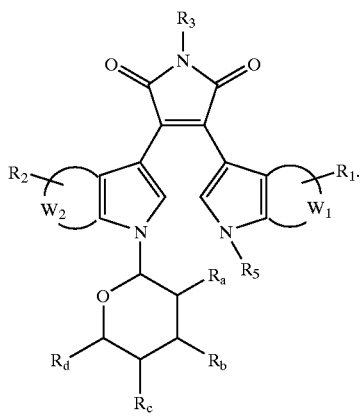
(IF)

9. A compound of claim 1, which is a compound of formula (IG):

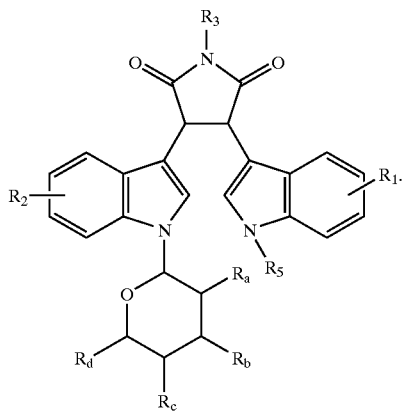

(IG)

10. A compound of claim 1, which is a compound of formula (IH):

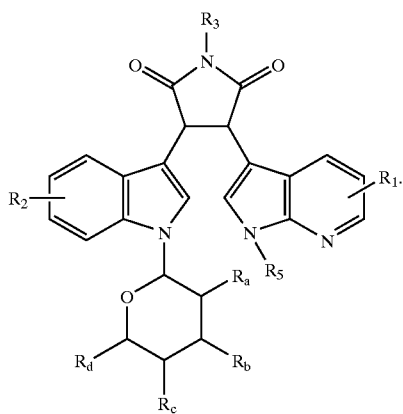

(IH)

11. A compound of claim 1, which is a compound of formula (IJ):

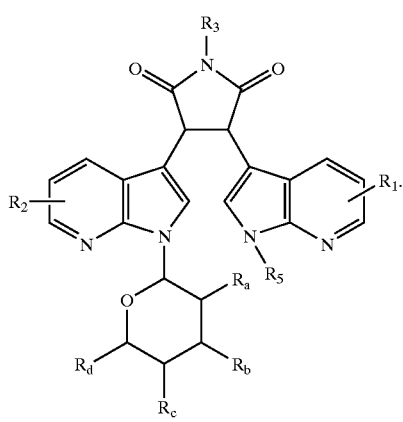

(IJ)

12. A compound of claim 4, wherein pyridine is unsubstituted.

13. A compound of claim 1, wherein $R_4$ represents a group of formula:

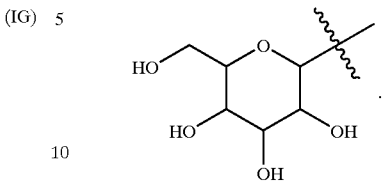

14. A compound of claim 1, wherein $R_2$ represents hydrogen.

15. A compound of claim 1, wherein $R_1$ represents hydrogen, halogen or nitro.

16. A compound of claim 1, which is selected from:
6-methyl-13-(β-D-glucopyranosyl)-12,13-dihydro-5H-pyrido[3',2':4,5]pyrrolo[2,3-a]-pyrrolo[3,4-c]carbazole-5,7(6H)-dione,
6-methyl-12-(β-D-glucopyranosyl)-12,13-dihydro-5H-pyrido[2,3-b]pyrido[3',2':4,5]-pyrrolo[3,2-g]pyrrolo[3,4-e]indole-5,7(6H)-dione,
9-bromo-6-methyl-13-(β-D-glucopyranosyl)-12,13-dihydro-5H-pyrido[3',2':4,5]pyrrolo[2,3-a]pyrrolo[3,4-c]carbazole-5,7(6H)-dione,
13-(β-D-glucopyranosyl)-12,13-dihydro-5H-pyrido[3',2':4,5]pyrrolo[2,3-a]pyrrolo-[3,4-c]carbazole-5,7(6H)-dione,
9-nitro-13-(β-D-glucopyranosyl)-12,13-dihydro-5H-pyrido[3',2':4,5]pyrrolo[2,3-a]-pyrrolo[3,4-c]carbazole-5,7(6H )-dione,
12-(β-D-glucopyranosyl)-12,13-dihydro-5H-pyrido[2,3-b]pyrido[3',2':4,5]-pyrrolo[3,2-g]pyrrolo[3,4-e]indole-5,7(6H)-dione, and
and 1-methyl-3-[1-(β-D-glucopyranosyl)-1H-pyrrolo[2,3-b]pyrid-3-yl]-4-(1H-pyrrolo[2,3b]pyrid-3-yl)-1H-pyrrole-2,5-dione.

17. A method for treating a living animal body afflicted with a condition selected from leukaemia, neuorblastoma, epidermoid carcinoma, and cell lung cell carcinoma, comprising the step of administering to the living animal body an amount of a compound of claim 1, which is effective for alleviation of the condition.

18. A pharmaceutical compositionm, comprising as active principle an effective amount of a compound of claim 1, together with one or more pharmaceutically acceptable excipients or vehicles.

19. A compound of formula (IX):

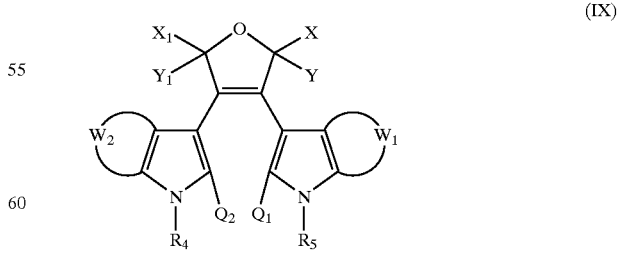

(IX)

wherein:
$W_1$, $W_2$, together with the carbon atoms to which they are bonded, each represent phenyl or pyridyl, wherein at least one of the groups $W_1$ or $W_2$ represents pyridyl, X represents a group selected from hydrogen, hydroxy, linear or branced $(C_1-C_6)$alkoxy, mercapto and linear or branched $(C_1-C_6)$alkylthio, Y represents hydrogen, or X and Y, together with carbon atom carrying them, form carbonyl or thiocarbonyl, $X_1$ represents a group selected from hydrogen, hydroxy, linear or branched $(C_1-C_6)$alkoxy, mercapto and linear or branched $(C_1-C_6)$alkylthio, $Y_1$ represents hydrogen, or $X_1$ and $Y_1$, together with carbon atom carrying them, form carbonyl or thiocarbonyl, $Q_1$, $Q_2$ represents hydrogen, or $Q_1$ and $Q_2$, together with carbon atoms carrying them, form an aromatic bond, $R_4$ represents a group of formula (a):

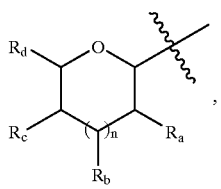

(a)

wherein:

$R_a$, $R_b$ and $R_c$, which may be indentical or different, each represent, independently of the others, a group selected from hydrogen, halogen, hydroxy, linear or branched $(C_1-C_6)$alkoxy, aryloxy, aryl-$(C_1-C_6)$alkoxy in which the alkoxy moiety may be linear or branched, linear or branched $(C_1-C_6)$alkyl, aryl-$(C_1-C_6)$alkyl in which the alkyl moiety may be linear or branched, aryl, —$NR_6R_7$, azido, —N=$NR_6$, wherein $R_6$ and $R_7$, which may be identical or different, each represents a group selected form hydrogen, linear or branched $(C_1-C_6)$alkyl aryl, aryl-$(C_1-C_6)$alkyl groups in which the alkyl moiety may be linear or branched, or $R_6$ and $R_7$, together with the nitrogen atom carrying them, form a saturated, monocyclic or bicyclic heterocycle that has from 5 to 10 ring atoms, and which optionally contains in the ring system a second hetero atom selected from oxygen and nitogen, and which is optionally substituted by a group selected from linear or branched $(C_1-C_6)$ alkyl, aryl, aryl-$(C_1-C_6)$alkyl in which moiety may be linear or branched, hydroxy, linear or branched $(C_1-C_6)$alkoxy, amino, linear or branched mono-$(C_1-C_6)$alkylamino, and di-$(C_1-C_6)$alkylamino in which the alkyl moieties may be linear or branched, —O—C(O)—$R_8$, wherein $R_8$ represents a linear or branched $(C_1-C_6)$alkyl optionally substituted by one or more groups selected from halogen, hydroxy, amino, linear or branched $(C_1-C_6)$alkylamino, and di-$(C_1-C_6)$alkylamino in which the alkyl moieties may be linear or branched, aryl, aryl-$(C_1-C_6)$alkyl in which the alkyl moiety may be linear or branched, cycloalkyl or heterocyclolakyl, $R_d$ represents a methylidene or a group of formula -$U_1$-$R_a$ wherein $U_1$ represents single bond or a methylene and $R_a$ is as defined hereinbefore, n is 0 or 1, $R_5$ represents a group selected from a hydrogen, linear or branched $(C_1-C_6)$alkyl, aryl-$(C_1-C_6)$alkyl in which the alkyl moiety may be linear or branched, arylsulphonyl, linear or branched $(C_1-C_6)$alkyloxycarbonyl, —$OR_6$ and —C(O)—$R_6$ (wherein $R_6$ is as defined hereinbefore), or $R_4$ and $R_5$ together represent, a group of formula (b) or (c):

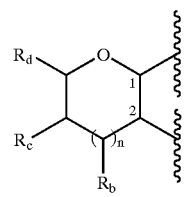

(b)

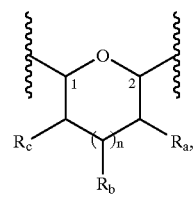

(c)

wherein:

carbon atom 1 is bonded to nitrogen of the ring (A) and carbon atom 2 is bonded to nitrogen of the ring (B), $R_a$, $R_b$, $R_c$ and $R_d$ are as defined hereinbefore, n is 0 or 1, with the proviso that in case $Q_1$ and $Q_2$ together form an aromatic bond, its enantiomers and diasteroisomers, and addition salts thereof with a pharmaceutically acceptable acid or base, aryl being understood to mean a phenyl, naphthyl, dihydronaphthyl, tetrahydronaphthyl, indenyl or indanyl, each of those groups being optionally substituted by one or more identical or different groups selected from halogen, linear or branched $(C_1-C_6)$alkyl, linear or branched $(C_1-C_6)$trihaloalkyl, hydroxy, linear or branched $(C_1-C_6)$alkoxy, and amino optionally substituted by one or two linear or branched $(C_1-C_6)$alkyl.

20. The method of claim 17, wherein the living animal body is a human.

* * * * *

UNITED STATES PATENT AND TRADEMARK OFFICE
CERTIFICATE OF CORRECTION

PATENT NO. : 7,001,906 B2
APPLICATION NO. : 10/481991
DATED : February 21, 2006
INVENTOR(S) : Michelle Prudhomme et al.

It is certified that error appears in the above-identified patent and that said Letters Patent is hereby corrected as shown below:

Column 39, Formula (IG):

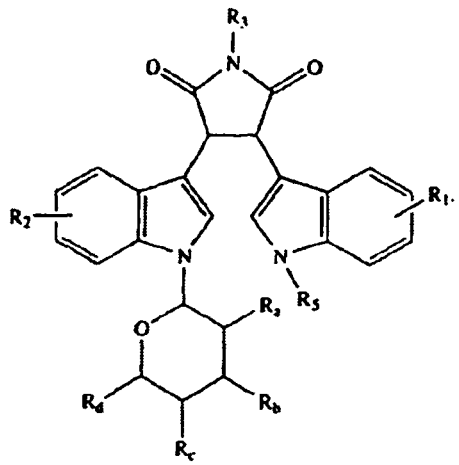

SHOULD BE

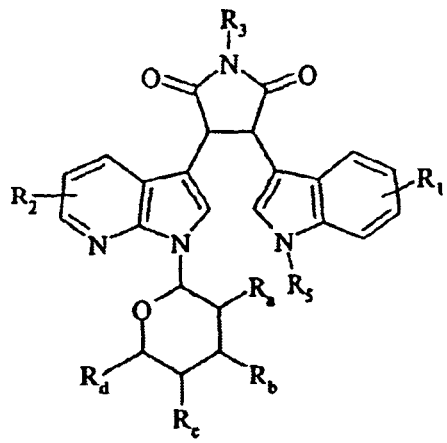

Column 40, Line 43: "and cell lung cell carcinoma," should be -- and small cell lung carcinoma, --.

Column 40, Line 46: " compositionm," should be -- composition, --.

UNITED STATES PATENT AND TRADEMARK OFFICE
CERTIFICATE OF CORRECTION

PATENT NO. : 7,001,906 B2
APPLICATION NO. : 10/481991
DATED : February 21, 2006
INVENTOR(S) : Michelle Prudhomme et al.

It is certified that error appears in the above-identified patent and that said Letters Patent is hereby corrected as shown below:

Column 41, Line 2: "branced" should be -- branched --.

Column 41, Line 50: "which moiety" should be -- which the alkyl moiety --.

Signed and Sealed this

Twenty-first Day of November, 2006

JON W. DUDAS
*Director of the United States Patent and Trademark Office*